United States Patent [19]
Chabrecek et al.

[11] Patent Number: 6,087,412
[45] Date of Patent: Jul. 11, 2000

[54] POLYMERS BASED ON BLOCK COPOLYMERS

[75] Inventors: Peter Chabrecek, Clayton, Australia; Dieter Lohmann, Münchenstein; Kurt Dietliker, Fribourg, both of Switzerland

[73] Assignee: Novartis AG, Basel, Switzerland

[21] Appl. No.: 08/860,132

[22] PCT Filed: Dec. 27, 1995

[86] PCT No.: PCT/CH95/00309

§ 371 Date: Sep. 12, 1997

§ 102(e) Date: Sep. 12, 1997

[87] PCT Pub. No.: WO96/21167

PCT Pub. Date: Jul. 11, 1996

[30] Foreign Application Priority Data

Dec. 30, 1994 [CH] Switzerland ............... 3967/94
Dec. 30, 1994 [CH] Switzerland ............... 3968/94

[51] Int. Cl.[7] ............... G02C 7/02; G02C 7/04; C08F 2/50; C08F 287/00
[52] U.S. Cl. ............... 522/35; 522/39; 522/42; 522/36; 522/904; 522/135; 522/136; 522/137; 522/142; 522/144; 522/148; 351/159; 351/160 R; 351/160 H; 525/90; 525/92 C
[58] Field of Search ............... 522/35, 904, 39, 522/42, 182, 36, 135, 136, 137, 142, 144, 148; 351/159, 160 R, 160 H

[56] References Cited

U.S. PATENT DOCUMENTS

| | | | |
|---|---|---|---|
| 4,977,293 | 12/1990 | Hatton et al. | 558/153 |
| 5,070,170 | 12/1991 | Robertson et al. | 528/25 |
| 5,334,681 | 8/1994 | Mueller et al. | 526/243 |
| 5,371,147 | 12/1994 | Spinelli et al. | 525/288 |
| 5,527,925 | 6/1996 | Chabrecek et al. | 549/430 |
| 5,532,112 | 7/1996 | Kohler et al. | 430/281.1 |
| 5,612,389 | 3/1997 | Chabrecek et al. | 522/35 |

FOREIGN PATENT DOCUMENTS

| | | |
|---|---|---|
| 1262488 | 9/1988 | Australia . |
| 0281941A2 | 3/1988 | European Pat. Off. . |
| 0302831A1 | 7/1988 | European Pat. Off. . |
| 0632329A1 | 6/1994 | European Pat. Off. . |

*Primary Examiner*—Susan W. Berman
*Attorney, Agent, or Firm*—R. Scott Meece; Robert J. Gorman, Jr.

[57] ABSTRACT

The invention relates to crosslinked polymers, which are polymerisation products of a polymerisable mixture that comprises the following components:

a) a macromer of formula C

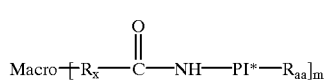

$$\text{Macro}\left[\text{R}_x-\overset{\overset{\text{O}}{\|}}{\text{C}}-\text{NH}-\text{PI}^*-\text{R}_{aa}\right]_m \quad (C)$$

wherein Macro is an m-valent radical of a macromer from which the number m of groups $Rx_x$—H has been removed, each $R_x$, independently of the others, is a bond, —O—, —$NR_N$— or —S— wherein $R_N$ is hydrogen or lower alkyl, PI* is a bivalent radical of a photoinitiator, $R_{aa}$ is the moiety of a photoinitiator that forms the less reactive free radical on cleavage of the photoinitiator, and m is an integer from 1 to 100, b) a copolymerisable vinyl monomer and c) a copolymerisable crosslinker.

The polymers are suitable especially for the production of mouldings, such as for contact lenses.

15 Claims, No Drawings

POLYMERS BASED ON BLOCK COPOLYMERS

The invention relates to novel polymers based on segmented copolymers, for example block copolymers, that are suitable especially for the production of mouldings, and also to mouldings comprising such polymers, and to the use of the polymers in the production of mouldings and to methods of producing the polymers and the mouldings. Preferred mouldings are ophthalmic lenses, especially contact lenses. The polymers are distinguished from known polymers inter alia by the fact that they contain radicals of photo-initiators incorporated at the interfaces of the blocks. The coupling of the blocks is carried out in a photochemical reaction that allows the segment length of the terminal or pendant polymer blocks being grown on to be substantially controlled. According to the invention a segmented copolymer is to be understood as being a block copolymer, graft copolymer, especially a comb copolymer or star copolymer.

The segmented copolymers according to the invention correspond to the general formula I

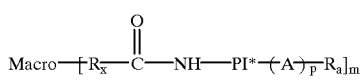 (I)

wherein Macro is an m-valent radical of a macromer from which the number m of groups $R_x$—H has been removed, each $R_x$, independently of the others, is a bond, —O—, —$NR_N$— or —S— wherein $R_N$ is hydrogen or lower alkyl, PI* is a bivalent radical of a photoinitiator, A is a substituted bivalent 1,2-ethylene radical derivable from a copolymerisable vinyl monomer by replacing the vinyl double bond by a single bond, each $R_a$, independently of the others, is a monovalent group that is suitable to act as a polymerisation chain-reaction terminator, and p, independently of m, is an integer from 3 to 500, and m is an integer from 1 to 100.

The segmented copolymers of formula I according to the invention may be built up from the following constituents: a macromer of formula A:

 (A)

wherein Macro, $R_x$ and m are as defined above except that $R_x$ is other than a bond, secondly a photoinitiator of formula B

 (B)

wherein PI* is as defined above and $R_{aa}$ is the moiety of a photoinitiator that forms the less reactive free radical on cleavage of the photoinitiator, and thirdly a vinyl monomer incorporated as component "A" into the segmented copolymer, wherein A is as defined above.

The macromer of formula A suitable according to the invention has a number m of groups —$R_x$H, which groups are hydroxy groups (including those that are a component of a carboxy group —COOH), amino groups or lower alkylamino groups (including those that are a component of an amide group —$CONR_N$) or mercapto groups. Those groups are co-reactive with the isocyanate group of the photoinitiator of formula B. A macromer of formula A is suitably reacted with m mol equivalents of the photoinitiator of formula B to form a macromer of formula (C)

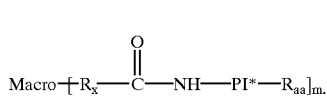 (C)

The macromer of formula C so formed, which contains m photoinitiators of formula B bonded via a bridge —O—CO—NH—, —CO—NH—, —$NR_N$—CO—NH—, —CO—$NR_N$—CO—NH— or —S—CO—NH—, is reacted in a further step with p mol equivalents of a vinyl monomer incorporated as component "A" into the copolymer of formula I. Chain-reaction termination is effected, for example, by the less reactive free radical of the photoinitiator $R_{aa}$ of formula B or by other suitable chain-reaction terminators present in the reaction mixture under the reaction conditions, such as H free radicals or OH free radicals or free radicals formed from solvents. The symbol $R_a$ is preferably the component $R_{aa}$ of the photoinitiator of formula B.

The definition "bond" for $R_x$ is applicable only in the case where an OH group in the macromer is present as a component of a COOH group. A COOH group reacts with an isocyanate group with the removal of $CO_2$ and with the formation of a bond "—CO—NH—". Only in that case is $R_x$ a bond in the reaction product, but not in a starting material containing the group "$R_x$—H".

The index p is preferably a number from 5 to 200, especially a number from 10 to 100.

The index m is preferably a number from 2 to 15, especially a number from 2 to 5.

The groups bonded to the macromer of formula A, of which, depending on the meaning of the index m, there may be from 1 to 100, are either terminal or pendant, or terminal and pendant.

In an especially preferred embodiment, the macromer of formula A has two terminal groups $R_x$H. A segmented copolymer of formula I according to the invention formed therefrom, that is to say a block copolymer of formula I, is also especially preferred and is referred to in this invention as a tri-block copolymer: the central block is formed by the macromer to which two photoinitiators are bonded, and the two terminal blocks are formed essentially by the bivalent radical A.

In another preferred embodiment, the macromer of formula A has only pendant groups $R_x$H. A segmented copolymer of formula I according to the invention formed therefrom, that is to say a graft copolymer of formula I, is also preferred and is referred to in this invention as a comb polymer: the back or ridge of the comb is formed by the macromer, to which several photoinitiators are bonded in pendant manner, and the tines or teeth of the comb are formed essentially by the bivalent radicals A, which are bonded via the radical of the photoinitiator.

In another preferred embodiment, a cyclic macromer of formula A has pendant groups $R_x$H. A segmented copolymer of formula I according to the invention formed therefrom, that is to say a graft copolymer of formula I, is also preferred and is referred to in this invention as a star polymer: the central point of the star is formed by the macromer, to which several photoinitiators are bonded in pendant manner, and the arms of the star are formed essentially by the bivalent radicals A, which are bonded via the radical of the photoinitiator.

It is significant that all the copolymers of formula I according to the invention, and the crosslinked polymers obtainable therefrom, differ from conventional copolymers and polymers in a surprising manner in respect of their properties. One reason for this is because the chain length of the vinyl monomers (see —(A)$_p$— in formula I) can be substantially controlled in accordance with the invention. Also, the copolymers of formula I are surprisingly free, or at least substantially free, of the homopolymers of the respective vinyl monomer used, such as are frequently formed with other free radical macroinitiators described in the literature. These advantageous properties are transferred to the polymers according to the invention in the course of their preparation.

The segmented copolymers according to the invention may be reacted or further processed selectively to produce secondary products. Attention is drawn especially to the fact that the uncrosslinked copolymers of formula I can be incorporated in a simple manner into crosslinked polymers, for example by the reaction of a compound of formula C with the vinyl monomer in question being carried out in the presence of a crosslinker. In addition to such a crosslinking, or as an alternative thereto, copolymers of formula I according to the invention may be modified if they contain reactive groups in the moiety —(A)$_p$— according to formula I.

The crosslinked polymers according to the invention are accordingly polymerisation products of a polymerisable mixture that comprises the following components:

a) a macromer of formula C

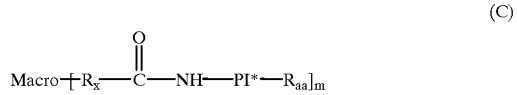

(C)

wherein Macro is an m-valent radical of a macromer from which the number m of groups R$_x$—H has been removed, each R$_x$, independently of the others, is a bond, —O—, —NR$_N$— or —S— wherein R$_N$ is hydrogen or lower alkyl, PI* is a bivalent radical of a photoinitiator, R$_{aa}$ is the moiety of a photoinitiator that forms the less reactive free radical on cleavage of the photoinitiator, and m is an integer from 1 to 100, b) a copolymerisable vinyl monomer and c) a crosslinker.

The polymers according to the invention are furthermore polymerisation products obtained by reacting the above-mentioned components a), b) and c) with one another in a manner known per se, and especially as described in detail below.

A macromer of formula C is used preferably in an amount of from 10 to 90% by weight, especially from 20 to 80% by weight, and a copolymerisable vinyl monomer is used like-wise preferably in an amount of from 10 to 90% by weight, especially from 20 to 80% by weight, the percentages by weight for the amounts of the components being relative to each other. A crosslinker is used preferably in an amount of up to 25% by weight, especially in an amount of up to 12.5% by weight, based on the sum of components a) and b). The preferred percentages apply also to crosslinker components obtained by subsequent modification of a copolymerised vinyl monomer.

A crosslinker, as mentioned as component c) above, may be a typical copolymerisable oligovinylic crosslinker as known from the prior art, which is added to the polymerisable mixture before polymerisation is initiated to produce the polymers according to the invention.

Alternatively, the crosslinker may be an oligofunctional compound that is co-reactive with reactive groups present in the —(A)$_p$— moiety. A reactive group in the —(A)$_p$— moiety is to be understood as meaning, for example, the OH group. A group, coreactive therewith, of an oligofunctional compound is, for example, the isocyanate group, the carboxy group, also in the form of an anhydride, and the epoxy group. Suitable oligofunctional compounds are accordingly, for example, diisocyanates, triisocyanates, dianhydrides, dicarboxylic acids or diepoxides. Another reactive group in the —(A)$_p$— moiety is, for example, the COOH group. Groups co-reactive therewith are, for example, the amino group or the hydroxy group. Suitable oligofunctional compounds are accordingly in that case, for example, diamines, diols or amino-alcohols. Further examples are known to the person skilled in the art.

A further possible crosslinking method comprises modifying reactive groups in the —(A)$_p$— moiety to convert them into crosslinkable groups. Examples of such modifications are given below.

Such reactive groups may be, for example, hydroxy groups which originate from a vinyl monomer, such as a hydroxy-lower alkyl (meth)acrylate, for example 2-hydroxyethyl methacrylate or 3-hydroxypropyl methacrylate, or from polyvinyl alcohol, which are subsequently reacted with a vinyl isocyanate, for example 2-isocyanatoethyl methacrylate. The C—C double bonds of a vinyl isocyanate incorporated in the manner so described allow crosslinking to form a polymer according to the invention and/or copolymerisation with further vinyl monomers or divinyl monomers.

Such reactive groups may be, for example, isocyanate groups, carboxy groups or epoxy groups which originate from a vinyl isocyanate, a vinylcarboxylic acid or a vinyl epoxy compound, for example from 2-isocyanatoethyl methacrylate, (meth)acrylic acid or glycidyl (meth)acrylate, which are subsequently reacted with a hydroxy-lower alkyl (meth)acrylate, for example 2-hydroxyethyl methacrylate or 3-hydroxypropyl methacrylate. The C—C double bonds of a hydroxy-lower alkyl (meth)acrylate incorporated in the manner so described allow crosslinking to form a polymer according to the invention and/or copolymerisation with further vinyl monomers or divinyl monomers.

Hereinbefore and hereinafter the term "(meth)acrylate" is used as an abbreviation for "methacrylate or acrylate".

As a result of all the properties mentioned hereinbefore, the polymers according to the invention are suitable for a wealth of intended uses as mouldings of varied kinds, such as as biomedical materials, for example implants, opthalmic lenses, especially artificial cornea, intraocular lenses or, more especially, contact lenses, or as medical instruments, devices, membranes and drug-delivery systems, or as coatings on inorganic or organic materials. In addition, the uncrosslinked segmented copolymers of formula I are not only suitable as starting materials for the polymers according to the invention but also excellently suitable as coating materials. With hydrophilic components "A", amphiphilic block, comb or star polymers are obtained that have surface-active properties and are, for example, suitable as emulsifiers.

The present invention accordingly relates to copolymers of formula I in uncrosslinked form, especially in the form of tri-block copolymers, comb polymers or star polymers. The present invention relates also to crosslinked polymers as defined above containing the mentioned components as main or sole components. The present invention relates furthermore to graft copolymers based on copolymers of formula I modified by grafting one or more vinyl monomers onto vinyl groups present in the (—A$_p$—) moiety or introduced into that moiety by way of reactive groups. The invention relates also to mouldings, especially contact lenses, manufactured from the said copolymers, polymers or graft copolymers. The invention relates also to processes for producing said copolymers, polymers or graft copolymers using the described starting materials and the process conditions given below. The invention relates also to the production of mouldings, especially contact lenses, from the mentioned copolymers, polymers or graft copolymers and to the use of the mentioned copolymers, polymers or graft copolymers in the production of mouldings, especially contact lenses.

The macromers of formula A are preferably oligomers or polymers having an average molecular weight of from 300 to 10,000 daltons and contain preferably at least 3, more preferably from 3 to 50, and especially from 5 to 20, structural units. As is known, the transition between oligomers and polymers is fluid and cannot be defined exactly. The polymers may contain from 50 to 10,000, more preferably from 50 to 5,000, structural units and may have an average molecular weight of from 10,000 to 2,000,000, preferably from 10,000 to 500,000. The oligomers and polymers may also contain up to 95 mol %, preferably from 5 to 90 mol %, comonomeric structural units having no active-H groups (this term has the same meaning here as "R$_x$H groups", which are as defined hereinbefore, with the proviso that R$_x$ is in this case other than a bond), based on the polymer.

The oligomers and polymers having active-H groups may be natural or synthetic oligomers or polymers.

Natural oligomers and polymers are, for example, oligo- and poly-saccharides or derivatives thereof, peptides, proteins, glycoproteins, enzymes and growth factors. Some examples are cyclodextrins, starch, hyaluronic acid, deacetylated hyaluronic acid, chitosan, trehalose, cellobiose, maltotriose, maltohexaose, chitohexaose, agarose, chitin, amylose, glucanes, heparin, xylan, pectin, galactan, polygalactosamine, glycosaminoglycanes, dextran, aminated dextran, cellulose, hydroxyalkylcelluloses, carboxyalkylcelluloses, heparin, fucoidan, chondroitin sulfate, sulfated polysaccharides, mucopolysaccharides, gelatin, casein, silk fibroin, zein, collagen, albumin, globulin, bilirubin, ovalbumin, keratin, fibronectin and vitronectin, pepsin, trypsin and lysozyme.

The synthetic oligomers and polymers may be substances containing the groups —COOH, —OH, —NH$_2$ or —NHR$_N$ wherein R$_N$ is lower alkyl, preferably C$_1$–C$_6$alkyl. They may be, for example, hydrolysed polymers of vinyl esters or ethers (polyvinyl alcohol); hydroxylated polydiolefins, e.g. polybutadiene, polyisoprene or chloroprene; polyacrylic acid and polymethacrylic acid and also polyacrylates, polymethacrylates, polyacrylamides or polymethacrylamides having hydroxyalkyl or aminoalkyl radicals in the ester group or amide group; polysiloxanes having hydroxyalkyl or aminoalkyl groups; polyethers of epoxides or glycidyl compounds and diols; polyvinylphenols or copolymers of vinylphenol and olefinic comonomers; and copolymers of at least one monomer from the group vinyl alcohol, vinylpyrrolidone, acrylic acid, methacrylic acid, or hydroxyalkyl- or aminoalkyl-containing acrylates, methacrylates, or acrylamide or methacrylamide, or hydroxylated diolefins, with ethylenically unsaturated comonomers, e.g. acrylonitrile, olefins, diolefins, vinyl chloride, vinylidene chloride, vinyl fluoride, vinylidene fluoride, styrene, α-methylstyrene, vinyl ethers and vinyl esters; or polyoxaalkylenes having terminal OH or aminoalkyloxy groups.

Preferred oligomers and polymers are, for example, cyclodextrins having a total of from 6 to 8 ring-configured glucose structural units, or hydroxyalkyl or aminoalkyl derivatives or glucose- or maltose-substituted derivatives, of which at least one structural unit corresponds to formula (V)

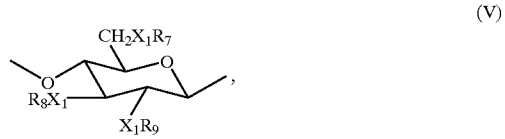

(V)

wherein R$_7$, R$_8$ and R$_9$ are each independently of the others H, C$_1$–C$_4$alkyl, especially methyl, C$_2$–C$_6$acyl, especially acetyl, C$_1$–C$_4$hydroxyalkyl, especially hydroxymethyl or 2-hydroxyeth-1-yl, C$_2$–C$_{10}$aminoalkyl or especially C$_2$–C$_4$ aminoalkyl, for example 2-aminoeth-1-yl or 3-aminoprop-1-yl or 4-aminobut-1-yl, X$_1$ is —O— or —NR$_{1B}$—, wherein, per cyclodextrin unit, a total of from 1 to 10 and preferably from 1 to 6 radicals X$_1$ may be —NR$_{1B}$— and the remaining radicals X$_1$ are —O—, wherein R$_{1B}$ is hydrogen or lower alkyl.

Other preferred oligomers and polymers are, for example, oligo- and poly-siloxanes having OH or NH$_2$ groups in alkyl, alkoxyalkyl or aminoalkyl terminal groups or sidechains. They may be random or block oligomers or block polymers. Oligomers and polymers to which greater preference is given are those which contain a) from 5 to 100 mol % structural units of formula (VII)

(VII)

and
b) from 95 to 0 mol % structural units of formula (VIII)

(VIII)

based on the oligomer or polymer, wherein R$_{11}$ is C$_1$–C$_4$alkyl, lower alkenyl, cyano-lower alkyl or aryl each unsubstituted or partly or completely substituted by F, and is preferably methyl, ethyl, vinyl, allyl, cyanopropyl or trifluoromethyl, R$_{12}$ is C2–C$_6$alkylene, preferably 1,3-propylene, —(CH$_2$)$_2$—(O—CH$_2$—CHCH$_3$—)$_2$—, —(CH$_2$)$_2$—(O—CH$_2$—CH$_2$)$_2$— or —(CH$_2$)$_2$—NH—(CH$_2$)$_2$—NH—, preferably —(CH$_2$)$_3$—(O—CH$_2$—CHCH$_3$—)$_2$— or -(CH$_2$)$_3$—NH—(CH$_2$)$_2$—NH—, wherein z is an integer from 2 to 4, R$_{14}$ has the same definitions as R$_{11}$ or is —R$_{12}$—X$_1$—H or —R$_{12}$—X$_1$—R$_{15}$—H, X$_1$ is —O— or —NH—, R$_{13}$ is a radical R$_x$H and R$_{15}$ is a direct bond or a group —C(O)—(CHOH)$_1$—CH$_2$—O— wherein r is 0 or an integer from 1 to 4.

Preferred oligomeric and polymeric siloxanes are also those of formula (X)

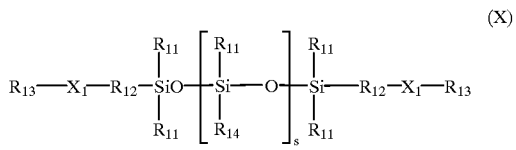

wherein $R_{11}$ is $C_1$–$C_4$alkyl, vinyl, allyl or phenyl each unsubstituted or partly or completely substituted by F, and is preferably methyl, $R_{12}$ is $C_2$–$C_6$alkylene, preferably 1,3-propylene, $R_{14}$ has the same definitions as $R_{11}$ or is —$R_{12}$—$X_1$—H or —$R_{12}$—$X_1$—$R_{15}$—H, $X_1$ is —O— or —NH—, s is an integer from 1 to 1000 and preferably from 1 to 150, $R_{13}$ is a radical $R_xH$, and $R_{15}$ is a direct bond or a group —C(O)—(CHOH)$_r$—CH$_2$—O— wherein r is 0 or an integer from 1 to 4. $X_1$ is preferably —NH—.

Other preferred oligomers and polymers are those based on oligovinyl and polyvinyl alcohol. They may be homopolymers having —CH$_2$CH(OH)—structural units or copolymers containing other monovalent or bivalent structural units of olefins.

More preferred are those oligomers and polymers which contain a) from 5 to 100 mol % structural units of formula (XI)

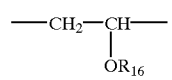

and b) from 95 to 0 mol % structural units of formula (XII)

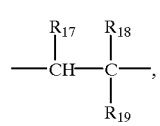

wherein $R_{16}$ is a radical $R_xH$, $R_{17}$ is H, $C_1$–$C_6$alkyl, —COOR$_{20}$ or —COO$^\ominus$, $R_{18}$ is H, F, Cl, CN or $C_1$–$C_6$alkyl, and $R_{19}$ is H, OH, $R_{10}$—H, F, Cl, CN, $R_{20}$—O—, $C_1$–$C_{12}$alkyl, —COO$^\ominus$, —COOR$_{20}$, —OCO—$R_{20}$, methylphenyl or phenyl, wherein $R_{10}$ is a direct bond, —($C_1$–$C_4$alkylene—O)— or —($C_2$–$C_{10}$alkylene-NH)—and $R_{20}$ is $C_1$–$C_{18}$alkyl, $C_5$–$C_7$cycloalkyl, ($C_1$–$C_{12}$alkyl)—$C_5$–$C_7$cycloalkyl, phenyl, ($C_1$–$C_{12}$alkyl)phenyl, benzyl or ($C_1$–$C_{12}$alkylbenzyl.

$R_{17}$ is preferably H. When $R_{17}$ is alkyl, it is preferably methyl or ethyl. When $R_{17}$ is —COOR$_{20}$, $R_{20}$ is preferably $C_1$–$C_{12}$alkyl, especially $C_1$–$C_6$alkyl.

When $R_{18}$ is alkyl, it is preferably $C_1$–$C_4$alkyl, e.g. methyl, ethyl, n-propyl or n-butyl. $R_{18}$ is preferably H, Cl or $C_1$–$C_4$alkyl.

When $R_{19}$ is the group $R_{20}$—O—, $R_{20}$ is preferably $C_1$–$C_{12}$alkyl, especially $C_1$–$C_6$alkyl. When $R_{19}$ is alkyl, it contains preferably from 1 to 6, especially from 1 to 4, carbon atoms. When $R_{19}$ is the group —COOR$_{20}$, $R_{20}$ is preferably $C_1$–$C_{12}$alkyl, especially $C_1$–$C_6$alkyl, or cyclopentyl or cyclohexyl. When $R_{19}$ is the group —OCO—$R_{20}$, $R_{20}$ is preferably $C_1$–$C_{12}$alkyl, especially $C_1$–$C_6$alkyl, or phenyl or benzyl.

In a preferred embodiment, $R_{17}$ is H, $R_{18}$ is H, F, Cl, methyl or ethyl, and $R_{19}$ is H, OH, F, Cl, CN, $C_1$–$C_4$alkyl, $C_1$–$C_6$alkoxy, $C_1$–$C_6$hydroxyalkoxy, —COO—$C_1$–$C_6$alkyl, —OOC—$C_1$–$C_6$alkyl or phenyl.

Especially preferred are those oligomers and polymers wherein $R_{17}$ is H, $R_{18}$ is H or methyl, and $R_{19}$ is H, OH, CN, methyl, OCH$_3$, O(CH$_2$)$_t$OH or —COOCH$_3$, and t is an integer from 2 to 6.

Another preferred group of oligomers and polymers comprises partly or completely hydroxyalkylated oligo- or polyacrylates or -methacrylates, or -acrylamides or -methacrylamides. They may contain, for example, from 5 to 100 mol % structural units of formula (XIII)

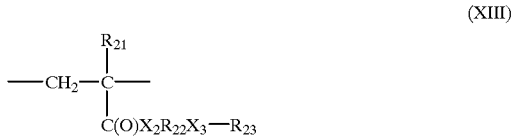

and from 95 to 0 mol % structural units of formula (XIV)

wherein $R_{21}$ is H or methyl, $X_2$ and $X_3$ are each independently of the other —O— or —NH—, $R_{22}$ is —(CH$_2$)$_c$—and c is an integer from 2 to 12, preferably from 2 to 6, $R_{23}$ is a radical of formula $R_xH$, $R_{17}$ and $R_{18}$ are as defined hereinbefore, and $R_{24}$ has the same definitions as $R_{19}$ or is —C(O)X$_2$R$_{22}$X$_3$H. For $R_{17}$, $R_{18}$ and $R_{19}$ the preferred definitions mentioned hereinbefore apply. For $X_2$ and $X_3$ the preferred definitions mentioned hereinbefore apply.

Other preferred oligomers and polymers are those consisting of polyalkylene oxides. They may, for example, be those of formula (XV) having identical or different repeating structural units —[CH$_2$CH($R_{26}$)—O]—

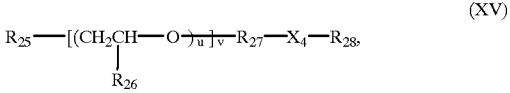

wherein $R_{25}$ is the group $R_{28}$—$X_4$— or is the radical of an alcohol or polyol having from 1 to 20 carbon atoms, the valency of that radical being from 1 to v, $R_{26}$ is H, $C_1$–$C_8$alkyl, preferably $C_1$–$C_4$alkyl and especially methyl, $R_{27}$ together with $X_4$ is a direct bond or $R_{27}$ is $C_2$–$C_6$alkylene, preferably $C_3$–C6alkylene and especially 1,3-propylene, $X_4$ is —O— or —NH—, $R_{28}$ is a radical of formula $R_xH$, u is a numerical value from 3 to 10,000, preferably from 5 to 5,000, especially from 5 to 1,000 and more especially from 5 to 100, and v is an integer from 1 to 6, preferably from 1 to 4.

$R_{25}$ may be a mono- to tetra-valent radical of an alcohol or polyol. When $R_{25}$ is the radical of an alcohol, $R_{25}$ is preferably linear or branched $C_3$–$C_{20}$-alkyl or -alkenyl, $C_3$–$C_8$- and especially $C_5$–$C_6$-cycloalkyl, —$CH_2$—($C_5$–$C_6$cycloalkyl), $C_6$–$C_{10}$aryl and especially phenyl and naphthyl, $C_7$–$C_{16}$aralkyl and especially benzyl and 1-phenyleth-2-yl. The cyclic or aromatic radicals may be substituted by $C_1$–$C_{18}$alkyl or $C_1$–$C_{18}$alkoxy.

When $R_{25}$ is the radical of a diol, $R_{25}$ is preferably branched or especially linear $C_3$–$C_{20}$-alkylene or -alkenylene and more preferably $C_3$–$C_{12}$alkylene, $C_3$–$C_8$- and especially $C_5$–$C_6$-cycloalkylene, —$CH_2$—($C_5$–$C_6$cycloalkyl)—, —$CH_2$–($C_5$–$C_6$cycloalkyl)—$CH_2$—, $C_7$–$C_{16}$-aralkylene and especially benzylene, —$CH_2$—($C_6$–$C_{10}$aryl)—$CH_2$- and especially xylylene. The cyclic or aromatic radicals may be substituted by $C_1$–$C_{12}$alkyl or $C_1$–$C_{12}$alkoxy.

When $R_{25}$ is a trivalent radical, it is derived from aliphatic or aromatic triols. $R_{25}$ is preferably a trivalent aliphatic radical having from 3 to 12 carbon atoms that is derived especially from triols having preferably primary hydroxy groups. Most preferably, $R_{25}$ is —$CH_2$(CH—)$CH_2$—, $HC(CH_2$—$)_3$ or $CH_3C(CH_2$—$)_3$.

When $R_{25}$ is a tetravalent radical, it is derived preferably from aliphatic tetrols. $R_{25}$ is in that case preferably $C(CH_2$—$)_4$.

Preferably, $R_{25}$ is a radical derived from Jeffamines (Texaco), a Pluriol, a Poloxamer (BASF) or poly(tetramethylene oxide).

Especially preferred are homo- and block oligomers and homo- and block polymers having structural units of the formula —[$CH_2CH_2$—O]— or [—$CH_2CH(CH_3)$—O]—.

Also suitable are fluorinated polyethers corresponding to formula (XVI)

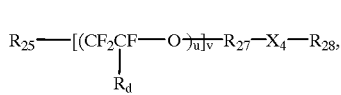

(XVI)

wherein $R_{27}$, $R_{28}$, $X_4$, u and v are as defined hereinbefore, $R_{25}$ is as defined hereinbefore or is the monovalent radical of a partially fluorinated or per-fluorinated alcohol having from 1 to 20, preferably from 1 to 12 and especially from 1 to 6, carbon atoms, or the bivalent radical of a partially fluorinated or per-fluorinated diol having from 2 to 6, preferably from 2 to 4 and especially 2 or 3, carbon atoms, and $R_d$ is F or perfluoroalkyl having from 1 to 12, preferably from 1 to 6 and especially from 1 to 4, carbon atoms. $R_d$ is especially —$CF_3$.

Other suitable oligomers and polymers are, for example, polyamines, such as polyvinylamine, or polyethyleneimines. Also suitable is poly-ε-lysine.

A suitable photoinitiator of formula B is in principle any photoinitiator that contains an isocyanate group. Such photoinitiators have already been described, for example, in EP-A-632 329. Suitable photoinitiators usually contain the structural unit

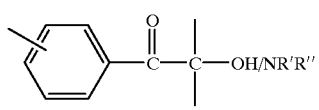

(in which "OH/NR'R''" indicates that the carbon atom in question carries either an OH group or an NR'R'' group wherein R' and R'' are each independently of the other linear or branched lower alkyl that may be substituted by $C_1$–$C_4$alkoxy; or aryl-lower alkyl or lower alkenyl; or R' and R'' together are —($CH_2)_z$—$Y_{11}$—($CH_2)_z$— wherein $Y_{11}$ is a direct bond, —O—, —S— or —$NR_{1B}$— and $R_{1B}$ is H or lower alkyl, and z is an integer from 2 to 4), which, on being suitably excited, forms two free radicals as a result of the bond between the benzoyl carbon and the sp$^3$ carbon being cleaved. Usually, the benzoyl free radical is the more reactive free radical, and that free radical generally initiates polymerisation. The symbol PI* from formula B therefore corresponds preferably to such a benzoyl free radical. That benzoyl free radical is substituted, as is known in the prior art, and according to the invention in addition contains an isocyanate group. It can be seen from the foregoing that the sp$^3$ carbon free radical is the less reactive free radical which, as a rule, does not assist in initiating polymerisation. Instead it reacts preferentially as a chain-reaction terminator. The symbol $R_{aa}$ from formula B therefore corresponds preferably to such an sp$^3$ carbon free radical.

Photoinitiators especially preferred in accordance with the invention are described below.

The functional photoinitiators of formula B used according to the invention are preferably compounds of formula IIa or IIb

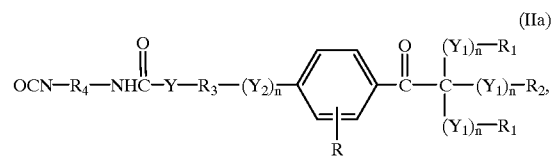

(IIa)

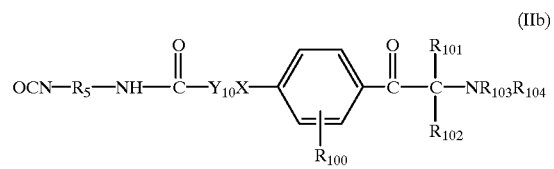

(IIb)

wherein Y is O, NH or $NR_{1A}$;

$Y_1$ is O;

$Y_2$ is —O—, —O—(O)C—, —C(O)—O— or —O—C(O)—O—;

each n independently of the others is 0 or 1;

R is H, $C_1$–$C_{12}$alkyl, $C_1$–$C_{12}$alkoxy or $C_1$–$C_{12}$alkylNH—;

$R_1$ and $R_2$ are each independently of the other H, linear or branched $C_1$–$C_8$alkyl, $C_1$–$C_8$—hydroxyalkyl or $C_6$–$C_{10}$aryl, or two groups $R_1$—$(Y_1)_n$— together are —($CH_2)_x$—, or the groups $R_1$—$(Y_1)_n$— and $R_2$—$(Y_1)_n$— together are a radical of the formula

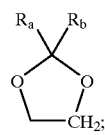

$R_3$ is a direct bond or linear or branched $C_1$–$C_8$alkylene that is unsubstituted or substituted by —OH and/or optionally interrupted by one or more groups —O—, —O—C(O)— or —O—C(O)—O—;

$R_4$ is branched $C_3$–$C_{18}$alkylene, unsubstituted or $C_1$–$C_4$alkyl- or $C_1$–$C_4$alkoxy-substituted $C_6$–$C_{10}$arylene, or unsubstituted or $C_1$–$C_4$alkyl- or $C_1$–$C_6$alkoxy-substituted $C_7$–$C_{18}$-aralkylene, unsubstituted or $C_1$–$C_4$alkyl- or $C_1$–$C_4$alkoxy-substituted $C_3$–$C_8$cycloalkylene, unsubstituted or $C_1$–$C_4$alkyl- or $C_1$–$C_4$alkoxy-substituted $C_3$–$C_8$cycloalkylene—$C_yH_{2y}$- or unsubstituted or $C_1$–$C_4$alkyl- or $C_1$–$C_4$alkoxy-substituted —$C_YH_{2y}$–($C_3$–$C_8$cycloalkylene)—$C_yH_{2y}$—;

$R_5$ independently has the same definitions as $R_4$ or is linear $C_3$–$C_{18}$alkylene;

$R_{1A}$ is lower alkyl;

x is an integer from 3 to 5;

y is an integer from 1 to 6;

$R_a$ and $R_b$ are each independently of the other H, $C_1$–$C_8$alkyl, $C_3$–$C_8$cycloalkyl, benzyl or phenyl;

with the provisos that n in the groups —$(Y_1)_n$—$R_1$ is 0 when $R_2$ is H; that not more than two $Y_1$s of the —$(Y_1)_n$— groups are O and n in the other —$(Y_1)_n$— groups is 0; and that n in the group —$(Y_2)_n$— is 0 when $R_3$ is a direct bond;

and wherein also

X is bivalent —O—, —NH—, —S—, lower alkylene or

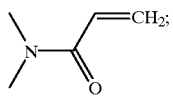

$Y_{10}$ is a direct bond or —O—$(CH_2)_y$— wherein y is an integer from 1to 6 and the terminal $CH_2$ group is linked to the adjacent X in formula (IIb);

$R_{100}$ is H, $C_1$–$C_{12}$alkyl, $C_1$–$C_{12}$alkoxy, $C_1$–$C_{12}$alkylNH— or —$NR_{1A}R_{1B}$ wherein $R_{1A}$ is lower alkyl and $R_{1B}$ is H or lower alkyl;

$R_{101}$ is linear or branched lower alkyl, lower alkenyl or aryl-lower alkyl;

$R_{102}$ independently of $R_{101}$ has the same definitions as $R_{101}$ or is aryl, or $R_{101}$ and $R_{102}$ together are —$(CH_2)_m$— wherein m is an integer from 2 to 6;

$R_{103}$ and $R_{104}$ are each independently of the other linear or branched lower alkyl that may be substituted by $C_1$–$C_4$alkoxy; or aryl-lower alkyl or lower alkenyl; or $R_{103}$ and $R_{104}$ together are —$(CH_2)_z$— wherein $Y_{11}$ is a direct bond, —O—, —S— or —$NR_{1B}$—and $R_{1B}$ is H or lower alkyl, and z is an integer from 2 to 4.

In a preferred embodiment, Y is O.

$R_{1A}$ as alkyl may be, for example, methyl, ethyl, n- or iso-propyl, n-, iso- or tert-butyl, pentyl or hexyl. $R_{1A}$ is preferably methyl.

The group R contains as alkyl, alkoxy or alkylNH- preferably from 1 to 6 and especially from 1 to 4 carbon atoms. Some examples are methyl, ethyl, n- or iso-propyl, n-, iso- or tert-butyl, pentyl, hexyl, octyl, decyl, dodecyl, methoxy, ethoxy, propoxy, butoxy and methylNH-. Most preferably, R is H.

$R_1$ as alkyl is preferably linear and contains preferably from 1 to 4 carbon atoms. Some examples are methyl, ethyl, n- or iso-propyl, n-, iso- or tert-butyl, pentyl, hexyl, heptyl and octyl. $R_1$ is especially methyl or ethyl. $R_1$ as aryl may be, for example, naphthyl or especially phenyl. When the two groups $R_1$—$(Y_1)_n$— together are —$(CH_2)_x$—, x is preferably 4 or especially 5. $R_1$ as hydroxyalkyl is preferably linear and contains preferably from 1 to 4 carbon atoms. Some examples are hydroxymethyl and 2-hydroxyeth-1-yl.

For $R_2$ the same preferred definitions as for $R_1$ apply. $R_2$ is preferably H, methyl or ethyl.

$R_a$ and $R_b$ are preferably each independently of the other H or $C_1$–$C_4$alkyl, for example methyl or ethyl.

In a preferred sub-group, $R_1$ is preferably ethyl and especially methyl, or the two groups $R_1$—$(Y_1)_n$— together are pentamethylene, n in the group —$(Y_1)_n$—$R_2$ is preferably 0, $R_2$ is preferably methyl, hydroxymethyl or H and R is H.

In another preferred embodiment, in the group —$(Y_1)_n$—$R_2$, $Y_1$ is O, n is 1 and $R_2$ is H. In this case, n in the groups $R_1$—$(Y_1)_n$— is especially 0.

$R_3$ as alkylene contains preferably from 1 to 6 and especially from 1 to 4 carbon atoms and the alkylene is preferably linear. Some examples are methylene, ethylene, 1,2- or 1,3-propylene, 1,2-, 1,3- or 1,4-butylene, pentylene, hexylene, heptylene and octylene. Methylene, ethylene, 1,3-propylene and 1,4-butylene are preferred. Most especially, $R_3$ is ethylene; or a direct bond, in which case n in the group —$(Y_2)_n$— is 0.

When $R_3$ is hydroxy-substituted alkylene it may be, for example, especially 2-hydroxy-1,3-propylene or also 2-hydroxy- 1,3- or -1,4-butylene. Alkylene interrupted by —O— and unsubstituted or substituted by —OH is, for example, —$CH_2CH_2$—O—$CH_2CH_2$—, —$CH_2CH_2$—O—$CH_2CH_2$—O—$CH_2CH_2$—, —$CH_2CH_2$—O—$CH_2CH_2$—O—$CH_2$—[—$CH(CH_3)CH_2$—O—$CH(CH_3)CH_2$—], —$CH(CH_3)CH_2$—O—$CH_2CH_2$—, —$CH(C_2H_5)CH_2$—O—$CH_2CH_2$—, [—$CH(C_2H_5)CH_2$—O—$CH(C_2H_5)CH_2$—] or —$CH_2CH_2CH_2CH_2$—O—$CH_2CH_2CH_2CH_2$—and —$CH_2CH(OH)CH_2$—O—$CH_2CH_2$—. Alkylene interrupted by —O—C(O)— or —C(O)—O— is, for example, —$CH_2CH_2$—C(O)—O—$CH_2$— or —$CH_2CH_2$—O—C(O)—$CH_2$—. Alkylene interrupted by —O—C(O)—O— is, for example, —$CH_2CH_2$—O—C(O)—O—$CH_2CH_2$— or —$CH_2CH_2$—O—C(O)—O—$CH_2$—.

The substituents $C_1$–$C_4$alkyl and $C_1$–$C_4$alkoxy are preferably methyl or ethyl and methoxy or ethoxy.

$R_4$ as branched alkylene contains preferably from 3 to 14 and especially from 4 to 10 carbon atoms. Examples of alkylene are 1,2-propylene, 2-methyl- or 2,2-dimethyl-1,3-propylene, 1,2-, 1,3- and 2,3-butylene, 2-methyl- or 2,3-dimethyl-1,4-butylene, 1,2-, 1,3- or 1,4-pentylene, 2-methyl- or 3-methyl- or 4-methyl- or 2,3-dimethyl- or 2,4-dimethyl- or 3,4-dimethyl- or 2,3,4-trimethyl- or 2,2,3-trimethyl- or 2,2,4-trimethyl- or 2,2,3,3-tetra -methyl- or 2,2,3,4-tetramethyl-1,5-pentylene, 1,2-, 1,3-, 1,4- or 1,5-hexylene, and 2-methyl- or 3-methyl- or 4-methyl- or 2,2-dimethyl- or 3,3-dimethyl- or 2,3-dimethyl- or 2,4-dimethyl- or 3,4-dimethyl- or 2,2,3-trimethyl- or 2,2,4-trimethyl- or 2,2,5-trimethyl- or 2,3,4-trimethyl- or 2,2,4,5-tetramethyl-1,6-hexylene. Further examples are disclosed in EP-A-632 329.

Some preferred branched alkylene radicals are 2,2-dimethyl-1,4-butylene, 2,2-dimethyl-1,5-pentylene, 2,2,3- or 2,2,4-trimethyl-1,5-pentylene, 2,2-dimethyl-1,6-hexylene, 2,2,3- or 2,2,4- or 2,2,5-trimethyl-1,6-hexylene, 2,2-dimethyl-1,7-heptylene, 2,2,3- or 2,2,4- or 2,2,5- or 2,2,6-trimethyl- 1,7-heptylene, 2,2-dimethyl-1,8-octylene, and 2,2,3- or 2,2,4- or 2,2,5- or 2,2,6- or 2,2,7-trimethyl-1, 8-octylene.

When $R_4$ is arylene, it is preferably naphthylene and especially phenylene. When the arylene is substituted, one substituent is preferably in the ortho-position with respect to an isocyanate group. Examples of substituted arylene are 1-methyl-2,4-phenylene, 1,5-dimethyl-2,4-phenylene, 1-methoxy-2,4-phenylene and 1-methyl-2,7-naphthylene.

$R_4$ as aralkylene is preferably naphthylalkylene and especially phenylalkylene. The alkylene group in the aralkylene contains preferably from 1 to 12, more preferably from 1 to 6 and especially from 1 to 4, carbon atoms. Most preferably, the alkylene group in the aralkylene is methylene or ethylene. Some examples are 1,3- or 1,4-benzylene, naphth-2-yl-7-methylene, 6-methyl- 1,3- or - 1,4-benzylene, 6-methoxy-1,3- or - 1,4-benzylene.

When $R_4$ is cycloalkylene, it is preferably $C_5$- or $C_6$-cycloalkylene that is unsubstituted or substituted by methyl. Some examples are 1,3-cyclobutylene, 1,3-cyclopentylene, 1,3- or 1,4-cyclohexylene, 1,3- or 1,4-cycloheptylene, 1,3- or 1,4- or 1,5-cyclooctylene, 4-methyl-1,3-cyclopentylene, 4-methyl-1,3-cyclohexylene, 4,4-dimethyl-1,3-cyclohexylene, 3-methyl- or 3,3-dimethyl-1,4-cyclohexylene, 3,5-dimethyl-1,3-cyclohexylene, 2,4-dimethyl-1,4-cyclohexylene.

When $R_4$ is cycloalkylene-$C_yH_{2y}$—, it is preferably cyclopentylene-$C_yH_{2y}$— or especially cyclohexylene-$C_yH_{2y}$— that is unsubstituted or substituted by preferably from 1 to 3 $C_1$–$C_4$alkyl groups, especially methyl groups. In the group —$C_yH_{2y}$—, y is preferably an integer from 1 to 4. More preferably, the group —$C_yH_{2y}$— is ethylene and especially methylene. Some examples are cyclopent-1-yl-3-methylene, 3-methyl-cyclopent-1-yl-3-methylene, 3,4-dimethyl-cyclopent-1-yl-3-methylene, 3,4,4-trimethyl-cyclopent-1-yl- 3-methylene, cyclohex-1-yl-3- or -4-methylene, 3- or 4- or 5-methyl-cyclohex-1-yl-3- or -4-methylene, 3,4- or 3,5-dimethyl-cyclohex-1-yl-3- or -4-methylene, 3,4,5- or 3,4,4- or 3,5,5-trimethyl-cyclohex-1-yl-3- or -4-methylene.

When $R_4$ is —$C_yH_{2y}$-cycloalkylene-$C_yH_{2y}$—, it is preferably —$C_yH_{2y}$-cyclopentylene-$C_yH_{2y}$— and especially —$C_yH_{2y}$-cyclohexylene-$C_yH_{2y}$— that is unsubstituted or substituted by preferably from 1 to 3 $C_1$–$C_4$alkyl groups, especially methyl groups. In the group —$C_yH_{2y}$—, y is preferably an integer from 1 to 4. More preferably, the groups —$C_yH_{2y}$— are ethylene and especially methylene. Some examples are cyclopentane-1,3-dimethylene, 3-methyl-cyclopentane-1,3-dimethylene, 3,4-dimethyl-cyclopentane-1,3-dimethylene, 3,4,4-trimethyl-cyclopentane-1,3-dimethylene, cyclohexane-1,3- or -1,4-dimethylene, 3- or 4- or 5-methyl-cyclohexane-1,3- or -1,4-dimethylene, 3,4- or 3,5-dimethyl-cyclohexane-1,3- or -1,4-dimethylene, or 3,4,5- or 3,4,4- or 3,5,5-trimethyl-cyclohexane-1,3- or -1,4-dimethylene.

When $R_5$ has the same definitions as $R_4$, the preferred definitions given hereinbefore for $R_4$ also apply. $R_5$ as linear alkylene contains preferably from 3 to 12 and especially from 3 to 8 carbon atoms. Some examples of linear alkylene are 1,3-propylene, 1,4-butylene, 1,5-pentylene, 1,6-hexylene, 1,7-heptylene, 1,8-octylene, 1,9-nonylene, 1,10-decylene, 1,11-undecylene, 1,12-dodecylene, 1,14-tetradecylene and 1,18-octadecylene.

A preferred definition of X is —O—, —NH—, —S— or lower alkylene. More preferably, X is —O— or —S— and especially —O—.

In a preferred definition of $Y_{10}$, the index y is from 1 to 5, more preferably from 2 to 4, and most preferably 2 or 3, so that $Y_{10}$ is, for example, ethyleneoxy or propyleneoxy. In another preferred definition, $Y_{10}$ is a direct bond, X then preferably being or containing at least one hetero atom.

The group $R_{100}$ as alkyl, alkoxy, alkylNH- or —$NR_{1A}R_{1B}$ contains preferably from 1 to 6 and especially from 1 to 4 carbon atoms. Some examples are methyl, ethyl, n- or isopropyl, n-, iso- or tert-butyl, pentyl, hexyl, octyl, decyl, dodecyl, methoxy, ethoxy, propoxy, butoxy, N,N-dimethylamino and N-methylamino. Most preferably, R is H. A preferred definition of —$NR_{1A}R_{1B}$ is N,N-dimethylamino, N-methylamino, N-methyl-N-ethylamino, N-ethylamino, N,N-diethylamino, N-isopropylamino or N,N-diisopropylamino.

$R_{101}$ is preferably allyl, benzyl or linear $C_1$–$C_4$alkyl, for example methyl or ethyl.

$R_{102}$ has preferably the same definitions as $R_{101}$ and is more preferably linear lower alkyl having from 1 to 4 carbon atoms and especially 1 or 2 carbon atoms. $R_{102}$ as aryl may be, for example, naphthyl or especially phenyl that is unsubstituted or substituted by lower alkyl or lower alkoxy. When $R_{101}$ and $R_{102}$ together are —$(CH_2)_m$—, m is preferably 4 or 5 and especially 5.

$R_{103}$ is preferably linear lower alkyl having from 1 to 4 carbon atoms, benzyl or allyl, and more preferably methyl or ethyl.

$R_{104}$ is preferably linear lower alkyl having from 1 to 4 carbon atoms and more preferably methyl or ethyl.

When $R_{103}$ and $R_{104}$ together are —$(CH_2)_z$—$Y_{11}$—$(CH_2)_z$—, $Y_{11}$ is preferably a direct bond, —O— or —N($CH_3$)— and most preferably —O—; z is preferably 2 or 3 and especially 2.

A preferred sub-group of compounds of formula IIa comprises those wherein in the groups $R_1$—$(Y_1)_n$—, n is 0, Y, $Y_2$ and $Y_1$ in the group $R_2$—$(Y_1)_n$— are each O, n in the group $R_2$—$(Y_1)_n$— is 0 or 1, $R_1$ is $C_1$–$C_4$alkyl or phenyl or the groups $R_1$—$(Y_1)_n$— together are tetramethylene or pentamethylene, $R_2$ is $C_1$–$C_4$alkyl or H, R is hydrogen, n in the group —$(Y_2)$—$_n$ is 0 or 1 and $R_3$ is linear or branched $C_2$–$C_4$alkylene, or is a direct bond, in which case n in the group —$(Y_2)$—$_n$ is 0, $R_4$ is branched $C_5$–$C_{10}$alkylene, phenylene or phenylene substituted by from 1 to 3 methyl groups, benzylene or benzylene substituted by from 1 to 3 methyl groups, cyclohexylene or cyclohexylene substituted by from 1 to 3 methyl groups, cyclohexyl-$C_yH_{2y}$— or —$C_yH_{2y}$-cyclohexyl-$C_yH_{2y}$—, or cyclohexyl-$C_yH_{2y}$— or —$C_yH_{2y}$-cyclohexyl-$C_yH_{2y}$— substituted by from 1 to 3 methyl groups, $R_5$ has the same definitions as $R_4$ or is linear $C_3$–$C_{10}$alkylene, and y is 1 or 2.

An especially preferred sub-group of compounds of formula IIa comprises those wherein in the groups $R_1$—$(Y_1)_n$— and —$(Y_2)$—$_n$, n is 0, Y, $Y_2$ and $Y_1$ in the group $R_2$—$(Y_1)_n$— are each O, n in the group $R_2$—$(Y_1)_n$— is 0 or 1, $R_1$ is methyl or phenyl or the groups $R_1$—$(Y_1)_n$— together are pentamethylene, $R_2$ is methyl or H, R is hydrogen, n in the group —$(Y_2)$—$_n$ is 1 and $R_3$ is ethylene or n in the group —$(Y_2)$—$_n$ is 0 and $R_3$ is a direct bond, $R_4$ is branched $C_6$–$C_{10}$alkylene, phenylene or phenylene substituted by from 1 to 3 methyl groups, benzylene or benzylene substituted by from 1 to 3 methyl groups, cyclohexylene or cyclohexylene substituted by from 1 to 3 methyl groups, cyclohexyl-$CH_2$— or cyclohexyl-$CH_2$— substituted by from 1 to 3 methyl groups, and $R_5$ has the same definitions as $R_4$ or is linear $C_5$–$C_{10}$alkylene.

A preferred sub-group of compounds of formula IIb comprises those wherein $R_{101}$ is linear lower alkyl, lower alkenyl or aryl-lower alkyl;

$R_{102}$ independently of $R_{101}$ has the same definitions as $R_{101}$ or is aryl;

$R_{103}$ and $R_{104}$ are each independently of the other linear or branched lower alkyl that may be substituted by $C_1$–$C_4$alkoxy; or aryl-lower alkyl or lower alkenyl; or $R_{103}$ and $R_{104}$ together are —$(CH_2)_z$—$Y_{11}$—$(CH_2)_z$— wherein $Y_{11}$ is a direct bond, —O—, —S— or —$NR_{1B}$— and $R_{1B}$ is H or lower alkyl, and z is an integer from 2 to 4; and $R_5$ is linear or branched $C_3$–$C_{18}$alkylene, unsubstituted or $C_1$–$C_4$alkyl- or $C_1$–$C_4$alkoxy-substituted $C_6$–$C_{10}$arylene, or unsubstituted or $C_1$–$C_4$alkyl- or $C_1$–$C_4$alkoxy-substituted $C_7$–$C_{18}$aralkylene, unsubstituted or $C_1$–$C_4$alkyl- or $C_1$–$C_4$alkoxy-substituted $C_{13}$–$C_{24}$arylenealkylenearylene, unsubstituted or $C_1$–$C_4$alkyl- or $C_1$–$C_4$alkoxy-substituted $C_3$–$C_8$cycloalkylene, unsubstituted or $C_1$–$C_4$alkyl- or $C_1$–$C_4$alkoxy-substituted $C_3$–$C_8$cycloalkylene-$C_yH_{2y}$— or unsubstituted or $C_1$–$C_4$alkyl- or $C_1$–$C_4$alkoxy-substituted —$C_yH_{2y}$—($C_3$–$C_8$cycloalkylene)-$C_yH_{2y}$— wherein y is an integer from 1 to 6.

A preferred sub-group of compounds of formula IIb comprises those wherein

X is bivalent —O—, —NH—, —S— or —$(CH_2)_y$—;

$Y_{10}$ is a direct bond or —O—$(CH_2)_y$— wherein y is an integer from 1 to 6 and the terminal $CH_2$ group is linked to the adjacent X in formula (IIb);

$R_{100}$ is H, $C_1$–$C_{12}$alkyl or $C_1$–$C_{12}$alkoxy;

$R_{101}$ is linear lower alkyl, lower alkenyl or aryl-lower alkyl;

$R_{102}$ independently of $R_{101}$ has the same definitions as $R_{101}$ or is aryl, or $R_{101}$ and $R_{102}$ together are —$(CH_2)_m$— wherein m is an integer from 2 to 6;

$R_{103}$ and $R_{104}$ are each independently of the other linear or branched lower alkyl that may be substituted by $C_1$–$C_4$alkoxy; or aryl-lower alkyl or lower alkenyl; or $R_{103}$ and $R_{104}$ together are —$(CH_2)_z$—$Y_{11}$—$(CH_2)_z$— wherein $Y_{11}$ is a direct bond, —O—, —S— or —$NR_{1B}$— and $R_{1B}$ is H or lower alkyl, and z is an integer from 2 to 4; and $R_5$ is branched $C_6$–$C_{10}$alkylene, phenylene or phenylene substituted by from 1 to 3 methyl groups, benzylene or benzylene substituted by from 1 to 3 methyl groups, cyclohexylene or cyclohexylene substituted by from 1 to 3 methyl groups, or cyclohexylene-$CH_2$— or cyclohexylene-$CH_2$— substituted by from 1 to 3 methyl groups.

An especially preferred sub-group of compounds of formula IIb comprises those wherein $R_{101}$ is methyl, allyl, toluylmethyl or benzyl, $R_{102}$ is methyl, ethyl, benzyl or phenyl, or $R_{101}$ and $R_{102}$ together are pentamethylene, $R_{103}$ and $R_{104}$ are each independently of the other lower alkyl having up to 4 carbon atoms or $R_{103}$ and $R_{104}$ together are —$CH_2CH_2OCH_2CH_2$—, and $R_5$ is branched $C_6$–$C_{10}$alkylene, phenylene or phenylene substituted by from 1 to 3 methyl groups, benzylene or benzylene substituted by from 1 to 3 methyl groups, cyclohexylene or cyclohexylene substituted by from 1 to 3 methyl groups, or cyclohexylene-$CH_2$— or cyclohexylene-$CH_2$— substituted by from 1 to 3 methyl groups.

The groups $R_4$ and $R_5$ are especially groups that reduce the reactivity of the OCN group, this being achieved essentially by steric hindrance or electronic influences at at least one adjacent carbon atom. Preferably, $R_4$ and $R_5$ are therefore, inter alia, asymmetric radicals, for example alkylene that is branched in the α-position or especially the β-position with respect to the OCN group, or cyclic hydrocarbon radicals that are substituted as defined in at least one of the α-positions.

In the context of this invention, a copolymerisable vinyl monomer is to be understood as meaning especially a monomer that contains a vinyl group and has already been mentioned in connection with copolymers used for contact lenses. A vinyl group is to be understood in this context not as meaning exclusively the vinyl grouping "—CH=$CH_2$" but as meaning generally any grouping that has a carbon-carbon double bond. Especially preferred definitions of the word "vinyl" in vinyl monomers will become clear from the following explanations in connection with compounds of formula III. Copolymerisable vinyl monomers in the sense of this invention have already been disclosed, for example, in EP-A-374 752, EP-A-417 235 and EP-A-455 587.

The monomers used as starting materials to prepare component A of formula I for the block copolymers, polymers or contact lenses of the invention, are especially compounds of formula III

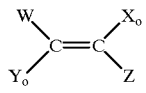
(III)

which, symbolised by the letters A, are incorporated into the block copolymer of formula I in the form of the partial formula IV

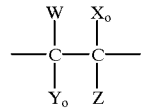
(IV)

wherein the substituents W, $X_0$, $Y_0$ and Z are defined as follows: three of those substituents are hydrogen and the fourth substituent is selected from acyl, halogen, a heterocyclic radical and aryl, or two of those substituents are hydrogen, a third is lower alkyl and the fourth substituent is selected from acyl, halogen, a heterocyclic radical and aryl, or two of those substituents are hydrogen and the other two substituents together form a hydrocarbon bridge that is uninterrupted or is interrupted by one or two hetero atoms, or the other two substituents are each independently acyl. The monomers of formula III are either hydrophilic vinyl monomers or hydrophobic vinyl monomers.

Aryl is especially an aromatic hydrocarbon radical having from 6 to 15 carbon atoms, such as phenyl or phenyl substituted by one or more, especially up to three, radicals of the kind lower alkyl, lower alkoxy, halogen, amino or hydroxy. Examples are phenyl and tolyl.

Halogen is especially chlorine, bromine or fluorine, but may also be iodine.

A heterocyclic radical is especially a 5- or 6-membered aromatic or saturated ring having one or two hetero atoms, such as oxygen or nitrogen atoms, especially having one or two nitrogen atoms. Lactams are also included.

A hydrocarbon bridge that is uninterrupted or interrupted by one or two hetero atoms is especially lower alkylene or lower alkylene interrupted by oxygen or by nitrogen. Lower alkylene interrupted by nitrogen may also be substituted, for example by lower alkyl. Examples are 1,3-propylene, 2-aza-1,3-propylene and N-methyl-2-aza-1,3-propylene.

Acyl is carboxy, aroyl, cycloalkanoyl or alkanoyl and is especially carboxy, unsubstituted or substituted aryloxycarbonyl, unsubstituted or substituted cycloalkyloxycarbonyl or unsubstituted or substituted alkoxycarbonyl.

Aroyl is, for example, benzoyl or benzoyl substituted by one or more, especially up to three, radicals of the kind lower alkyl, lower alkoxy, halogen or hydroxy, but may also be phenylsulfonyl or phenyloxysulfonyl, or phenylsulfonyl or phenyloxysulfonyl substituted by lower alkyl, lower alkoxy, halogen or by hydroxy.

Alkanoyl is preferably lower alkanoyl and is, for example, acetyl, propanoyl or butanoyl.

Cycloalkanoyl is preferably cycloalkyloxycarbonyl having up to 8 carbon atoms and is, for example, cyclohexyloxycarbonyl.

Unsubstituted alkoxycarbonyl is preferably lower alkoxycarbonyl and is, for example, methoxycarbonyl, ethoxycarbonyl, propyloxycarbonyl, butoxycarbonyl, tert-butoxy-carbonyl, tert-butylmethyloxycarbonyl or 2-ethylhexyloxycarbonyl.

Unsubstituted aryloxycarbonyl is preferably phenyloxycarbonyl.

Substituted aryloxycarbonyl is preferably phenyloxycarbonyl substituted by one or more, especially up to three, radicals of the kind lower alkyl, lower alkoxy, halogen or hydroxy.

Substituted alkoxycarbonyl is substituted preferably by hydrophobic groups, such as halogen, for example fluorine, siloxane groups or hydrophilic groups, such as hydroxy, amino, mono- or di-lower alkylamino, isocyanato or by a lower alkylene glycol. Other definitions of substituted alkoxycarbonyl, and also of substituted aryloxycarbonyl and substituted cycloalkyloxycarbonyl, are indicated implicitly by the following description of especially suitable vinyl monomers of formula III.

The hydrophilic vinyl monomers that can be used in accordance with the invention are preferably acrylates and methacrylates of formula III wherein W and $Y_0$ are hydrogen, $X_0$ is hydrogen or methyl and Z is a group —$Z^1$—$Z^2$ wherein $Z^1$ is —COO— bonded via oxygen to $Z^2$ and $Z^2$ is a hydrocarbon radical having from 1to 10 carbon atoms that is mono- or poly-substituted by a water-solubilising group, such as carboxy, hydroxy or tert-amino, for example tert-lower alkylamino having from 1to 7 carbon atoms per lower alkyl group, a polyethylene oxide group having from 2 to 100 repeating units, preferably from 2 to 40 repeating units, or a sulfate, phosphate, sulfonate or phosphonate group, for example a correspondingly substituted alkyl, cycloalkyl or phenyl radical or a combination of such radicals, such as phenylalkyl or alkylcycloalkyl; also acrylamides and methacrylamides of formula III wherein W and $Y_0$ are hydrogen, $X_0$ is hydrogen or methyl and Z is aminocarbonyl or di-lower alkylaminocarbonyl; acrylamides and methacrylamides of formula III wherein W and $Y_0$ are hydrogen, $X_0$ is hydrogen or methyl and Z is monosubstituted aminocarbonyl substituted by one of the groups $Z^2$ defined above or by lower alkyl; maleates and fumarates of formula III wherein W and $X_0$ (or W and Z) are hydrogen, and $Y_0$ and Z (or $X_0$ and $Y_0$) are each independently of the other a group —$Z^1$—$Z^2$ wherein $Z^1$ and $Z^2$ are as defined above; crotonates of formula III wherein W and $X_0$ are hydrogen, $Y_0$ is methyl and Z is a group —$Z^1$—$Z^2$ wherein $Z^1$ and $Z^2$ are as defined above; vinyl ethers of formula III wherein W, $X_0$ and $Y_0$ are hydrogen, $Y_0$ is methyl and Z is a group —$Z^1$—$Z^2$ wherein $Z^1$ is oxygen and $Z^2$ is as defined above; vinyl-substituted five- or six-membered heterocycles having one or two nitrogen atoms and also N-vinyl-lactams, such as N-vinyl-2-pyrrolidone, of formula III wherein W, $X_0$ and $Y_0$ are hydrogen and Z is a five- or six-membered heterocyclic radical having one or two nitrogen atoms, as well as the radical, bonded via nitrogen, of a lactam, for example the nitrogen-bonded radical of 2-pyrrolidone; and vinylically unsaturated carboxylic acids of formula III having a total of from 3 to 10 carbon atoms, such as methacrylic acid, crotonic acid, fumaric acid or cinnamic acid.

Preference is given, for example, to hydroxy-substituted $C_2$–$C_4$alkyl (meth)acrylates, five- to seven-membered N-vinyl-lactams, N,N-di-$C_1$–$C_4$alkyl(meth)acrylamides and vinylically unsaturated carboxylic acids having a total of from 3 to 5 carbon atoms.

Water-soluble monomers that can be used include: 2-hydroxyethyl, 2- and 3-hydroxypropyl, 2,3-dihydroxypropyl, polyethoxyethyl and polyethoxypropyl acrylates and methacrylates and the corresponding acrylamides and methacrylamides, acrylamide and methacrylamide, N-methyl-acrylamide and -methacrylamide, bisacetone-acrylamide, 2-hydroxyethylacrylamide, dimethyl-acrylamide and -methacrylamide and also methylolacrylamide and -methacrylamide, N,N-dimethyl- and N,N-diethyl-aminoethyl acrylate and methacrylate and the corresponding acrylamides and methacrylamides, N-tert-butylaminoethyl methacrylate and methacrylamide, 2- and 4-vinylpyridine, 4- and 2-methyl-5-vinyl-pyridine, N-methyl-4-vinylpyridine, 1-vinyl- and 2-methyl-1-vinyl-imidazole, dimethylallylamine and methyldiallylamine and also para-, meta- and ortho-aminostyrene, dimethylaminoethylvinyl ether, N-vinylpyrrolidone and 2-pyrrolidinoethyl methacrylate, acrylic and methacrylic acid, itaconic acid, cinnamic acid, crotonic acid, fumaric acid, maleic acid and the hydroxy-lower alkyl mono- and di-esters thereof, such as 2-hydroxyethyl and di(2-hydroxy)ethyl fumarate, maleate and itaconate, and also 3-hydroxypropylbutyl fumarate and di-polyalkoxyalkyl fumarates, maleates and itaconates, maleic acid anhydride, N-methylmaleic acid imide, sodium acrylate and methacrylate, 2-methacryloyloxyethylsulfonic acid, 2-acrylamido-2-methylpropanesulfonic acid, 2-phosphatoethyl methacrylate, vinylsulfonic acid, phenyl vinylsulfonate, sodium vinylsulfonate, p-styrenesulfonic acid, sodium p-styrenesulfonate and allylsulfonic acid, N-vinyl-pyrrolidone, N-vinylpyridone, N-vinylcaprolactam, and also the quaternised derivatives of cationic monomers, obtained by quaternisation with selected alkylating agents, for example halogenated hydrocarbons, such as methyl iodide, benzyl chloride or hexadecyl chloride, epoxides, such as glycidol, epichlorohydrin or ethylene oxide, acrylic acid, dimethyl sulfate, methyl sulfate and propanesultone.

A more complete list of water-soluble monomers that can be used in connection with this invention can be found in: R. H. Yocum and E. B. Nyquist, Functional Monomers, volume 1, pages 424–440 (M. Dekker, N.Y. 1973).

Preferred hydrophilic vinyl monomers are 2-hydroxyethyl methacrylate. 3-hydroxypropyl methacrylate, N-vinyl-2-pyrrolidone, polyethylene glycol methacrylate, especially having an ethylene glycol content of a molecular weight of approximately 400, N,N-dimethylacrylamide, and also acrylic and methacrylic acid.

Suitable as hydrophobic vinyl monomers that may be used in accordance with the invention are, for example: acrylates and methacrylates of formula III wherein W and Y. are hydrogen, $X_0$ is hydrogen or methyl and Z is a group $—Z^1—Z^3$ wherein $Z^1$ is —COO— bonded via oxygen to $Z^3$ and $Z^3$ is a linear or branched aliphatic, a cycloaliphatic or an aromatic group having from 1 to 21 carbon atoms, for example a correspondingly substituted alkyl, cycloalkyl or phenyl radical or a combination of such radicals, such as phenylalkyl or alkylcycloalkyl, which may contain ether or thioether bonds, sulfoxide or sulfone groups or a carbonyl group; or $Z^3$ is a heterocyclic group that contains oxygen, sulfur or nitrogen atoms and 5 or 6 or, if it is bicyclic, up to 10, ring atoms, or a polypropylene oxide or poly-n-butylene oxide group having from 2 to 50 recurring alkoxy units, or $Z^3$ is an alkyl group having from 1 to 12 carbon atoms that contains halogen atoms, especially fluorine atoms, or $Z^3$ is a siloxane group having from 1 to 6 Si atoms; acrylamides and methacrylamides of formula III wherein W and $Y_0$ are hydrogen, $X_0$ is hydrogen or methyl and Z is monosubstituted aminocarbonyl substituted by a group $Z^3$ as defined above; maleates and fumarates of formula III wherein W and $Y_0$ (or W and Z) are hydrogen and $Y_0$ and Z (or $X_0$ and $Y_0$) are each independently of the other a group $—Z^1—Z^3$ wherein $Z^1$ and $Z^3$ are as defined above; itaconates of formula III wherein W and $Y_0$ are hydrogen, XO is a group $—Z^1—Z^3$ wherein $Z^1$ and $Z^3$ are as defined above, and Z is a group $—CH_2—Z^1—Z^3$ wherein $Z^1$ and $Z^3$ are as defined above; crotonates of formula III wherein W and $X_0$ are hydrogen and $Y_0$ is methyl and Z is a group $—Z^1—Z^3$ wherein $Z^1$ and $Z^3$ are as defined above; vinyl esters of formula III wherein W. $Y_0$ and $X_0$ are hydrogen and Z is a group $—Z^1—Z^3$ wherein $Z^1$ is —COO— bonded via carbon to $Z^3$ and $Z^3$ is as defined above; vinyl ethers of formula III wherein W, $X_0$ and $Y_0$ are hydrogen and Z is a group $—Z^1—Z^3$ wherein $Z^1$ is oxygen and $Z^3$ is as defined above.

Special preference is given to $C_1$–$C_4$alkyl esters or $C_5$–$C_7$cycloalkyl esters of vinylically unsaturated carboxylic acids having from 3 to 5 carbon atoms.

The following are examples of suitable hydrophobic monomers: methyl, ethyl, propyl, isopropyl, butyl, isobutyl, tert-butyl, ethoxyethyl, methoxyethyl, benzyl, phenyl, cyclohexyl, trimethylcyclohexyl, isobornyl, dicyclopentadienyl, norbornylmethyl, cyclododecyl, 1,1,3, 3-tetramethylbutyl, n-butyl, n-octyl, 2-ethylhexyl, decyl, dodecyl, tridecyl, octadecyl, glycidyl, ethylthioethyl, furfuryl and tri-, tetra- and penta-siloxanylpropyl acrylates and methacrylates, and the corresponding amides; N-(1,1-dimethyl-3-oxobutyl)-acrylamide; mono- and di-methyl fumarate, maleate and itaconate; diethyl fumarate; isopropyl and diisopropyl fumarate and itaconate; mono- and di-phenyl and methylphenyl fumarate and itaconate; methyl and ethyl crotonate; methyl vinyl ether and methoxyethyl vinyl ether; vinyl acetate, vinyl propionate, vinyl benzoate, acrylonitrile, vinylidene chloride, styrene, α-methylstyrene and tert-butylstyrene.

Preferred hydrophobic vinyl monomers are methyl methacrylate, n-butyl methacrylate, isopropyl methacrylate, isobutyl methacrylate, cyclohexyl methacrylate and mixtures thereof.

Of the afore-mentioned vinyl monomers, two special types of hydrophobic vinyl monomers are worthy of special mention in connection with the invention, those being siloxane monovinyl components and fluorine-containing vinyl compounds.

Especially preferred siloxane monovinyl components are compounds of formula III wherein W and $Y_0$ are hydrogen, $X_0$ is hydrogen or methyl and Z is a group $—Z^1—Z^4$ wherein $Z^1$ is —COO— bonded via oxygen to $Z^4$ and $Z^4$ is silyl-lower alkyl mono- or poly-substituted, for example tri- to nona-substituted, by tri-lower alkylsilyloxy. Silyl-lower alkyl in this context is to be understood as meaning a lower alkyl radical substituted by one or more silicon atoms, the free valencies of which radical are saturated at the silicon atoms especially by tri-lower alkylsilyloxy. Individual compounds to which special attention is drawn are, for example, tris(trimethylsiloxy)silylpropyl methacrylate and tris-(tris(trimethylsiloxy)siloxy)silylpropyl methacrylate.

Especially preferred fluorine-containing vinyl compounds are compounds of formula III wherein W and $Y_0$ are hydrogen, $X_0$ is hydrogen or methyl and Z is a group $—Z^1—Z^5$ wherein $Z^1$ is —COO— bonded via oxygen to $Z^5$ and $Z^5$ is fluorine-substituted alkyl, especially lower alkyl. Specific examples are 2,2,2-trifluoroethyl methacrylate, 2,2, 3,3-tetra-fluoropropyl methacrylate, 2,2,3,3,4,4,5,5-octafluoropentyl methacrylate and hexafluoroisopropyl methacrylate.

As has already been mentioned, copolymers of formula I that are especially preferred are tri-block copolymers, comb polymers and star polymers. In the case of all three types of copolymer of formula I, but especially in the ase of tri-block copolymers, special preference is given to those in which Macro is the radical of a polysiloxane or of a fluorinated polyether and the moiety A is derived from a hydrophilic vinyl monomer containing a reactive group. The reactive group is especially hydroxy or isocyanato. Examples of vinyl monomers that contain such groups are hydroxy-lower alkyl (meth)-acrylates or an isocyanato-lower alkyl (meth) acrylate, such as, especially, hydroxyethyl methacrylate or isocyanatoethyl methacrylate.

Preference is given also to copolymers of formula I, especially tri-block copolymers, in which Macro is the radical of a polysiloxane or of a fluorinated polyether and the moiety A is derived from a hydrophilic vinyl monomer that does not contain any reactive groups. Such a vinyl monomer is especially a vinyl-lactam, especially N-vinylpyrrolidone. Preference is given also to copolymers of formula I, especially tri-block copolymers, in which Macro is the radical of a hydrophilic macromer, as defined above, and the moiety A is derived from a hydrophobic vinyl monomer.

As already mentioned, the polymers according to the invention are preferably prepared using as starting materials a compound of formula C and a vinyl monomer in the presence of a crosslinker.

Suitable crosslinkers are especially oligo-olefinic, especially diolefinic, monomers, e.g. allyl acrylate and methacrylate, ethylene glycol, diethylene glycol, triethylene glycol, tetraethylene glycol and, generally, polyethylene oxide glycol diacrylates and dimethacrylates, 1,4-butanediol and poly-n-butylene oxide glycol diacrylates and dimethacrylates, propylene glycol and polypropylene oxide glycol diacrylates and dimethacrylates, thiodiethylene glycol diacrylate and dimethacrylate, di(2-hydroxyethyl)

sulfone diacrylate and dimethacrylate, neopentyl glycol diacrylate and dimethacrylate, trimethylolpropane tri- and tetraacrylate, pentaerythritol tri- and tetra-acrylate, divinylbenzene, divinyl ether, divinylsulfone, disiloxanyl-bis-3-hydroxypropyl diacrylate or methacrylate and related compounds. Ethylene glycol dimethacrylate is preferred.

Suitable crosslinkers also include oligovinyl macromers, for example divinyl macromers, as described, for example, in U.S. Pat. No. 4,136,250. Also suitable as crosslinkers in the context of the invention are oligovinylsiloxane compounds, for example bis(meth)acryloxy-lower alkylsiloxanes having up to 10 silicon atoms. Examples are 3,5-bis(3-methacryloxypropyl) -3,5-bis(trimethylsiloxy)- 1,1,1, 7,7,7-hexamethyltetrasiloxane and 1,3-dimethacryloxypropyl-tetramethyldisiloxane.

The starting materials used in the preparation of the copolymers, polymers and graft copolymers according to the invention, for example starting materials of formulae A, B and III and the crosslinkers, are known per se and/or are described herein.

The compounds of formula II can be prepared in a manner known per se by the reaction of diIsocyanatEs with the appropriate acid-H photoinitiators. The compounds are obtained in high yields and a high degree of purity, even when two differently reactive acid-H groups are present simultaneously in the photoinitiator, for example two OH groups. It is especially advantageous to use diusocyanates having isocyanate groups of different reactivity, because by that means the formation of isomers and diadducts can be substantially suppressed. The different reactivity can be achieved, for example, as described hereinbefore by means of steric hindrance. The different reactivity can also be achieved by masking one isocyanate group in the diusocyanate, for example with carboxvlic acids or hydroxy-lamine. The compounds of formula hIa are known from EP-A-632 329.

Compounds of formula (IIb) can be prepared by reacting a compound of formula IIc

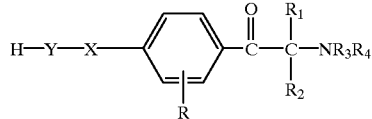

(IIc)

wherein X, Y, R, $R_1$, $R_2$, $R_3$ and $R_4$ are as defined hereinbefore, preferably in an inert organic solvent, with a diisocyanate of formula IId or with such a diisocyanate mono-masked where necessary, OCN—$R_5$—NCO (IId)

wherein $R_5$ is as defined hereinbefore.

Masking agents are known from urethane chemistry. They may be, for example, phenols (cresol, xylenol), lactams ($\epsilon$-caprolactam), oximes (acetoxime, benzophenone oxime), active-H methylene compounds (diethyl malonate, ethyl acetoacetate), pyrazoles or benzotriazoles. Masking agents are described, for example, by Z. W. Wicks, Jr. in Progress in Organic Coatings, 9 (1981), pages 3–28.

The starting materials of the formula IIc type are known and are described, for example, in EP-A-284 561 , EP-A-117 233 and EP-A-088 050.

Suitable inert solvents are aprotic, non-polar or polar solvents, such as, for example, hydrocarbons (petroleum ether, methylcyclohexane, benzene, toluene, xylene), halogenated hydrocarbons (chloroform, methylene chloride, trichloroethane, tetrachloroethane, chlorobenzene), ethers (diethyl ether, dibutyl ether, ethylene glycol dimethyl ether, diethylene glycol dimethyl ether, tetrahydrofuran (THF), dioxane), ketones (acetone, dibutyl ketone, methyl isobutyl ketone), carboxylic acid esters and lactones (ethyl acetate, butyrolactone, valerolactone), alkylated carboxylic acid amides (N,N-dimethylacetamide (DMA), N,N-dimethylformamide (DMF) or N-methyl-2-pyrrolidone (NMP)), nitriles (acctonitrile), sulfones and sulfoxides (dimethyl sulfoxide (DMSO), tetramethylene-sulfone). Polar solvents are preferably used.

The reactants are advantageously used in equimolar quantities. The reaction temperature may, for example, be from 0 to 200° C. When using catalysts, the temperatures may advantageously be in the range from –20° to 60° C. and preferably in the range from –10° to 50° C. Suitable catalysts are, for example, metal salts, such as alkali metal salts, of carboxylic acids, tertiary amines, for example $(C_1-C_6\text{alkyl})_3N$ (triethylamine, tri-n-butylamine), N-methylpyrrolidine, N-methylmorpholrine, N,N-dimethylpiperidine, pyridine and 1,4-diaza-bicyclooctane. Tin compounds have been found to be especially effective, especially alkyltin salts of carboxylic acids, such as, for example, dibutyltin dilaurate, or, for example, tin dioctoate.

If free NH groups are present in the compounds of formula IIc, those groups can initially be protected by suitable protecting groups during the reaction with a diiso-cyanate and subsequently freed again by removing the protecting groups. Suitable protecting groups are known to the person skilled in the art. Representative examples can be found, for example, in T. W. Greene, "Protective Groups in Organic Synthesis", Wiley Interscience, 1981.

The isolation and purification of the compounds prepared are carried out in accordance with known methods, for example extraction, crystallisation, re-crystallisation or chromatographic purification methods. The compounds are obtained in high yields and purity. The yields in the case of non-optimised processes may be more than 85% of the theoretical yields.

The reaction of a macromer of formula A with a photo-initiator of formula B can be effected simply and in a manner known per se in urethane chemistry.

The reaction between a reaction product, formed from a macromer of formula A and a photoinitiator of formula B, and a vinyl monomer being incorporated as component "A" into the copolymer can likewise be effected in a manner known per se. For example, a reaction product formed from a macromer of formula A and a photoinitiator of formula B may be copolymerised with a vinyl monomer, being incorporated as component "A" into the copolymer, in the absence or presence of a suitable solvent, at room temperature or at a temperature up to, at most, the boiling temperature of any solvent used. A suitable solvent is, for example, a hydrocarbon, such as hexane, benzene or toluene, or an ether, such as diethyl ether or tetrahydrofuran, or an alcohol, such as ethanol or isopropanol, or an amide, such as N-methylpyrrolidone, or dimethyl sulfoxide, or a mixture of several of those solvents. The purification is carried out in a manner known per se. In principle, the same conditions may be employed for the crosslinking reaction to form polymers or graft polymers according to the invention.

Suitable olefins for the mentioned graft polymerisation are, for example, acrylamide, N,N-dimethylacrylamide, methacrylamide, hydroxyethyl methacrylate, glyceryl methacrylate, oligoethylene oxide mono- and bis-acrylates, ethylene glycol dimethacrylate, methylene bisacrylamide, vinylcaprolactam, acrylic acid, methacrylic acid, fumaric acid monovinyl esters, vinyl trifluoroacetate and vinylene carbonate, it being possible for reactive esters to be hydrolysed subsequently where necessary.

In certain cases, it may be advantageous to use mixtures of two or more photoinitiators. Mixtures with known photoinitiators can, of course, also be used, for example mixtures with benzophenone, acetophenone derivatives, benzoin ethers or benzil ketals.

To accelerate the photopolymerisation, amines may be added, for example triethanolamine, N-methyl-diethanolamine, p-dimethylaminobenzoic acid ethyl ester or Michler's ketone. The action of the amines can be intensified by the addition of aromatic ketones of the benzophenone type.

The photopolymerisation can also be accelerated by the addition of photosensitizers, which shift or broaden the spectral sensitivity. These are especially aromatic carbonyl compounds, for example derivatives of benzophenone, thioxanthone, anthraquinone and 3-acylcoumarin, and 3-(aroylmethylene)-thiazolines.

The effectiveness of a photoinitiator can be increased by the addition of titanocene derivatives having fluoro-organic radicals, as are described in EP-A-122 223 and EP-A- 186 626, for example in an amount of from 1to 20%. Examples of such titanocenes are bis(methylcyclopentadienyl)-bis(2,3,6-trifluorophenyl)titanium, bis(cyclopentadienyl)-bis(4-dibutylamino-2,3 ,5 ,6-tetrafluoropheny l)titanium, bis(methylcyclopentadienyl)-2-(trifluoromethyl)phenyl-titanium isocyanate, bis(cyclopentadienyl)-2-(trifluoromethyl)phenyl-titanium trifluoroacetate and bis(methylcyclopentadienyl)-bis(4-decyloxy-2,3,5,6-tetrafluorophenyl)titanium. Liquid u.-aminoketones are especially suitable for those mixtures.

Mouldings, especially contact lenses, may be produced in a manner known per se from the segmented copolymers according to the invention, and especially from the polymers according to the invention. For that purpose, for example, the polymers according to the invention are polymerised in a cylindrical mould and, after removal from the mould, the obtainable rods are divided into disks or buttons which can be further processed mechanically, especially by turning processes. In addition, the mouldings or lenses according to the invention may also be produced according to other methods that are known per se, such as casting in static moulds, spin casting, compression, deep-drawing, heat-moulding, turning or laser machining. Those process steps are known per se and accordingly do not require any detailed explanation for the person skilled in the art.

The production of the mouldings is carried out preferably under an inert atmosphere when open moulds are used. Oxygen is known to inhibit polymerisation and result in prolonged polymerisation times. If closed moulds are used to form the polymerisation product, then the moulds advantageously consist of inert materials of low oxygen permeability having non-adhesive properties. Examples of suitable mould materials are polytetrafluoroethylene, such as Teflon®, silicone rubber, polyethylene, polypropylene and polyester, such as Mylar®. If a suitable mould-release agent is used, it is also possible to employ moulds made of glass and metal.

Casting in static moulds may, for example if moulds having an inner curve and an outer curve are used, result in contact lenses directly. For example, by polymerisation in suitable moulds it is possible to produce contact lenses requiring no further processing ("full-mold" process) or having only one finished face ("semi-mold" process).

Spin-casting may also be employed according to the invention by introducing a solution of the starting materials of the invention into a spin-casting mould, which is then set in rotation. During rotation, the solvent evaporates. The finished contact lens, the dimensions of which can be controlled by the dimensions of the mould, the spinning speed and the viscosity of the solution introduced, remains in the mould.

Compression is effected in accordance with the invention, for example, by compression-moulding a sheet of the polymer according to the invention. A sheet of the polymer can be produced in a manner known per se, for example by casting a solution.

From a sheet produced, for example, as mentioned above, it is possible to produce a contact lens in a manner known per se by deep-drawing or heat-moulding.

Turning is also a possible last process step in the production of contact lenses of the invention. That step is used whenever a blank obtainable, for example, in accordance with one of the above-mentioned procedures requires further processing. Turning is to be understood as meaning the machining, known per se, of contact lens blanks. Appropriate blanks may be produced, for example, by extruding round rods and dividing them into sections, or by casting from a solution. The term "contact lens blank" includes in this context buttons or semi-mold products, for example inner curve blanks. Typical blanks have thicknesses of from 4 to 6 mm and diameters of from 10 to 17 mm, for example 12 or 14 mm. It may be necessary for soft materials to be frozen, especially below the softening point, before undergoing the relevant machining and, if necessary, for the temperatures required for that purpose to be maintained during the machining.

Laser machining may also be used in accordance with the invention, such machining being carried out on blanks, or on contact lenses produced according to one of the other procedures where they still require an additional fine machining of their surface.

The following Examples illustrate the subject of the invention without, for example, limiting it to the scope of the Examples. Percentages are by weight, unless expressly indicated to the contrary. In the following Examples, unless indicated to the contrary, temperatures are in degrees Celsius and molecular weights, as elsewhere in the description, are average molecular weights (symbol "Mw") unless expressly defined otherwise.

A-EXAMPLES

Praparation of Aza Photoinitiators

Example A1

2-Dimethylamino-2-benzyl-1-(4-(2-hydroxyethoxy)phenyl)-butan-1-one.

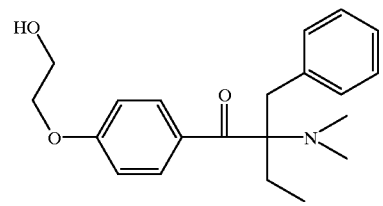

The preparation of the title compound is carried out in accordance with the synthesis described in EP-A-284 561.

Example A2

2-Ethyl-2-dimethylamino-1-(4-(2-hydroxyethoxy)phenyl)-pent-4-en-1-one.

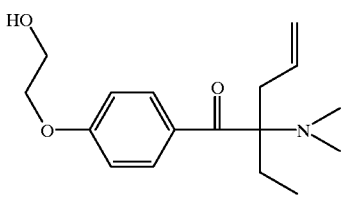

In analogy to Example A1, the title compound is prepared in quantitative yield. Yellowish crystals having a melting point of 80–82° C. remain.

Example A3
1-(4-(2-Hydroxyethylthio)phenyl)-2-methyl-2-morpholino-propan-1-one

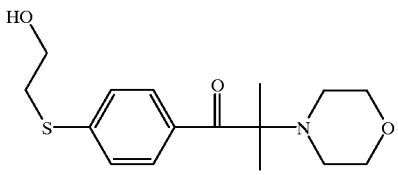

The preparation of the title compound is described in EP-A-088 050.

Example A4
1-(4-(2-Hydroxyethoxy)phenyl)-2-methyl-2-morpholino-propan-1-one.

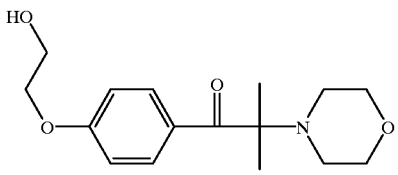

The title compound is prepared in analogy to Example A3.

Example A5

Preparation of the following compound:

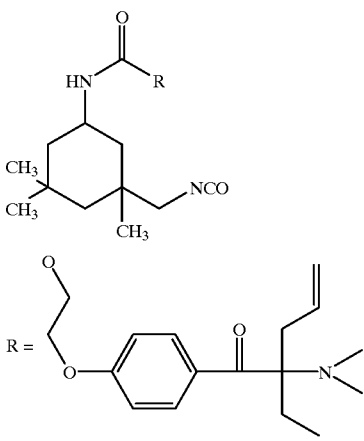

In a 100 ml flask fitted with a reflux condenser, a thermometer, a stirrer and a nitrogen inlet pipe, 2.92 g (10 mmol) of 2-ethyl-2-dimethylamino-1-(4-(2-hydroxyethoxy)-phenyl)-pent-4-en-1-one (from Example A2) are dissolved in 30 ml of dry methylene chloride and mixed with 2.22 g (10 mmol) of IPDI dissolved in 30 ml of dry methylene chloride. 2.0 mg of the catalyst DBTDL are added thereto and the mixture is stirred at RT for 72 hours. The course of the reaction is followed by TLC (eluant: toluene/acetone 6:1). The reaction solution is then stirred into water. The organic phase is removed and washed twice more with water. The organic phase is dried over MgSO$_4$ and concentrated using a rotary evaporator. The residue remaining is purified by column chromatography (toluene/acetone 6:1). 3.4 g (66%) of a yellow oil remain. The structure is verified by proton NMR, IR and elemental analysis.

Example A6

In analogy to Example A5, the following isocyanate is prepared from 1.17 g (4 mmol) of 1-(4-(2-hydroxyethoxy) phenyl)-2-methyl-2-morpholino-propan-1-one (from Example A4), 0.7 g (4 mmol) of 2,4-TDI, and DBTDL as catalyst in methylene chloride. After the addition of 50 ml of ether and 200 ml of petroleum ether to the reaction mixture, the target compound precipitates in crystalline form. It is filtered off, washed with petroleum ether and then dried under a vacuum. The compound below, having a melting point of 97–102° C., is obtained:

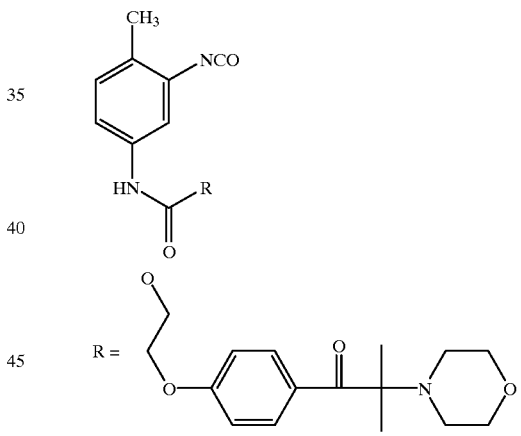

Examples A7 and A8

In analogy to Example A5 the following compounds are prepared:

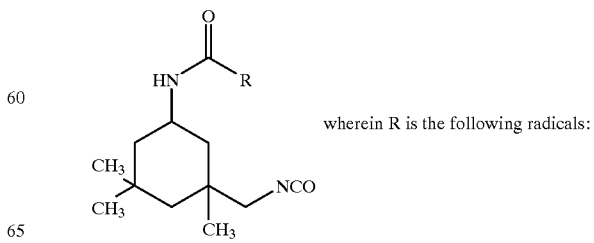

wherein R is the following radicals:

Example No. A7

R = 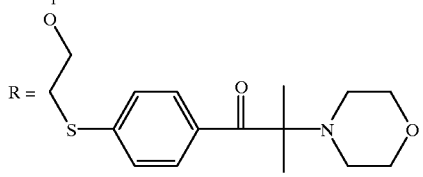

Example No. A8

R = 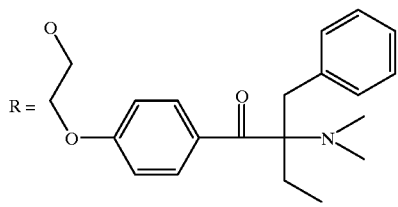

B-EXAMPLES: PREPARATION OF MACROPHOTOINITIATORS

Example B1

Preparation of an oligomeric photoinitiator:

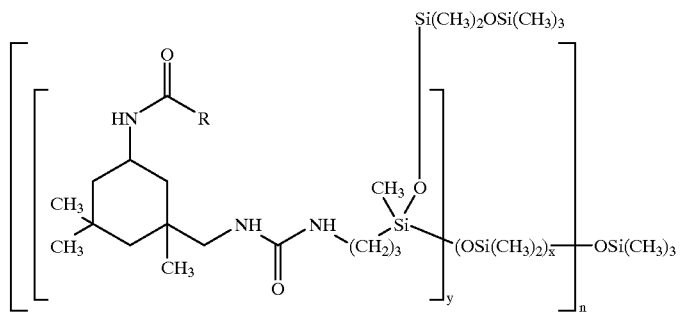

wherein R = 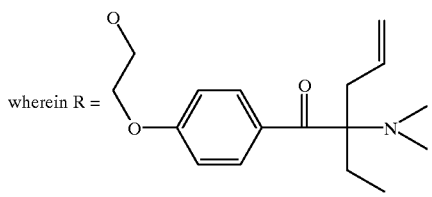

and x:y is approximately 27:1, and n is 5.

0.7 g (1.3 mmol) of the isocyanate from Example A5, 20 ml of dry methylene chloride and 2.55 g (0.51 m.equiv. $NH_2$/g) of aminoalkylpolysiloxane KF 8003 (Shin Etsu, Japan) are introduced into an apparatus according to Example A5. The reaction mixture is stirred for 2 hours at RT and for 20 minutes at 40° C. The solvent is then removed using a rotary evaporator. Solvent residues are removed from the residue under a high vacuum (40° C., 0.001 mbar (0.1 Pa)). The title compound is obtained in quantitative yield. No OCN bands are present in the IR spectrum.

Example B2

In analogy to Example B 1, an oligomeric photoinitiator with the structure according to Example B1 is prepared from 0.76 g (1.3 mmol) of isocyanate from Example A8 and 2.55 g (0.51 m.equiv. $NH_2$/g) of aminoalkylpolysiloxane KF 8003 (Shin Etsu, Japan), R having the following meaning:

R = 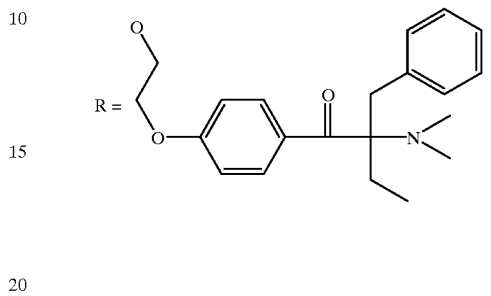

Example B3

In analogy to Example B1, an oligomeric photoinitiator with the following structure is prepared from 0.55 g (0.97 mmol) of isocyanate from Example A8 and 1.47 g (0.7 m.equiv. $NH_2$/g) of aminoalkylpolysiloxane X-22-161B (Shin Etsu, Japan):

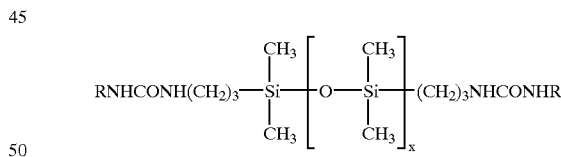

wherein x is approximately 38, and R corresponds to the radical of the title compound of Example A8 minus the isocyanate.

Example B4

In analogy to Example B 1, a solution of 1.0 g (1.95 mmol) of the isocyanate from Example A5 in 20 ml of dry acetonitrile is mixed with 2.24 g (0.84 m.equiv. $NH_2$/g) of Jeffamine ED 2001 (Texaco, USA) in 30 ml of dry acetonitrile and the mixture is stirred at RT for 24 hours. After working up, 3.2 g (99%) of the following photoinitiator are obtained:

R—NHCONH—$CHCH_3CH_2$-($OCHCH_3CH_2$)$_a$—($OCH_2CH_2$)$_b$—($OCHCH_3CH_2$)$_c$—NHCONH—R wherein a+c=2.5 and b=40.5, and R corresponds to the radical of the title compound of Example A5 minus the isocyanate.

Example B5

In an apparatus according to Example A5, 1.65 g of polyvinyl alcohol (PVA) (Serva® 03/20, molecular weight approximately 13 000) are dissolved in dry NMP at 80° C. under nitrogen. The solution is then cooled to RT and a solution of 1.0 g (1.88 mmol) of the isocyanate from Example A7 in 10 ml of dry NMP and 5 mg of DBTDL as catalyst are added thereto. The mixture is then heated at 40° C. for 48 hours. After that time, OCN can no longer be detected by IR at 2250 cm$^{-1}$. The reaction mixture is cooled to RT and 700 ml of diethyl ether are added, the product precipitating. The product is filtered, washed with diethyl ether and then dried under a high vacuum. 1.9 g of a wvhite product remain which, according to elemental analysis, contains 2.20% S. The proton NMR agrees with the following structure:

wherein n is approximately 10 and a:b=20: 1; and R corresponds to the radical of the title compound of Example A7 minus the isocyanate.

Examples B6, B7 and B8

In analogy to Example B5, two hydroxyalkyl-substituted polydimethylsiloxanes (KF-6002/KF-6001) and a dextran are reacted with the isocyanate from Example A7. The following parameters describe those compounds. The yields are in all cases about 90%. The sulfur content of those compounds is determined by means of combustion analysis (last column of the Table).

| Isocyanate from Example A7 | OH macromer | Solvent | S content (%) calc./found |
|---|---|---|---|
| 0.5 g (0.94 mmol) | KF-6002, Shin-Etsu, JP 1.5 g (0.63 equiv. OH/g) | THF | 1.50/1.38 |
| 0.5 g (0.94 mmol) | KF-6001, Shin-Etsu, JP 0.85 g (1.1 m.equiv. OH/g) | THF | 2.22/2.08 |
| 0.5 g (0.94 mmol) | Dextran 8, Serva AG 2.3 g, MW ≈ 8–12 000 | DMSO | 1.08/0.99 |

Example B9

In analogy to Example B5, 3.23 g of collagen (Serva 17440, MW≈80 000) are dissolved in DMSO for 12 hours and then 1.0 g (1.9 mmol) of isocyanate from Example A8 in 10 ml of DMSO is added. After being stirred for 72 hours at RT, the reaction mixture is diluted with 500 ml of methanol, whereupon the product precipitates. The product is filtered off and then washed repeatedly with dry THF. Drying is then carried out under a high vacuum (0.1 Pa, RT, 72 hours), yielding 2.8 g of a yellowish-white product, the IR spectrum and proton NMR of which agree with the expected structure.

Example 10

Preparation of a perfluoropolyether macromer (Fomblin ZDOL TX 1000). terminated at both ends with an isophorone diisocyanate-containing photoinitiator.

In a 100 ml flask fitted with a reflux condenser, a thermometer, a stirrer and a nitrogen inlet pipe, 4.46 g (0.01 mol) of the reactive photoinitiator (prepared according to Example A1 of EP-A-632 329) are dissolved in 10 g of dry THF and mixed with 5.73 g (0.005 mol) of Fomblin ZDOL TX 1000, Mw=1146 (Ausimont SpA, Milan, Italy). 2 mg of the catalyst DBTDL are added thereto and the mixture is stirred at 40° C. for 72 hours. After that reaction time, unreacted isocyanate can no longer be detected by IR spectroscopy.

After cooling to room temperature, the solvent is removed by concentration by evaporation using a rotary evaporator. A highly viscous, colourless oil is obtained which is freed of traces of solvent while under the high vacuum. The structure of the product is verified by means of the $^1$H-NMR spectrum.

C-Examples: Preparation of linear tri-block macromers

Example C1

In an amber round-bottomed flask fitted with a reflux condenser, a stirrer and an argon inlet pipe, 800 mg (0.2 mmol) of macrophotoinitiator from Example B6 according to EP-A-632 329 are dissolved in 4 ml of dry THF under argon. 2.95 g (20 mmol) of freshly distilled 2-hydroxypropyl methacrylate (2-HPMA) are added thereto and the mixture is stirred for 60 minutes. The flask with its contents is then immersed in liquid nitrogen for 10 minutes and the frozen solution is degassed for 15 minutes under reduced pressure (0.004 mbar). The vacuum is relieved with argon and the solution is heated to room temperature and gassed with argon for 15 minutes. After filtration through filters of 0.45 μm pore size, clean polypropylene moulds are filled with the solution under nitrogen (approximately 200 μl of solution per mould), closed and irradiated with UV light (12 mW/cm$^2$) for 20 minutes. The moulds containing the highly viscous polymer solution are then freed of THF in a drying cabinet at 40° C. Clear, transparent disks that are soluble in ethanol are obtained. The Mw of the tri-block macromer is 18 700 according to GPC analysis. It is striking that the GPC shows exclusively the formation of the tri-block copolymer and that no homopolymer of the vinyl monomer used is observed as secondary product.

Example C2

In analogy to Example C1, 1.96 g (0.5 mmol) of siloxane macrophotoinitiator B6 according to EP-A-632 329 are dissolved in 4 ml of dry THF under an inert gas atmosphere. 720 mg (5 mmol) of freshly distilled 2-HPMA are added thereto and the mixture is stirred for 60 minutes. The subsequent preparation of samples is the same as in Example C1. The Mw of this tri-block macromer corresponds to 7800 according to GPC analysis. It is striking that the GPC shows exclusively the formation of the tri-block copolymer and that no homopolymer of the vinyl monomer used is observed as secondary product.

Examples C3 to C9

In a manner corresponding to Example C I, further tri-block macromers having different macrophotoinitiators (see B-Examples) and having different types and compositions of comonomers are prepared. The following Tables contain the most important parameters (the abbreviations have the following meanings: HEMA=2-hydroxyethyl methacrylate, 2-HPMA=2-hydroxypropyl methacrylate, PME 400=polyethylene glycol (Mw 400) methacrylate, NVP=N-vinyl-2-pyrrolidone):

Example C3:

| | |
|---|---|
| macroinitiator ("MI"): | B10 according to EP-A-632 329, |
| comonomer: | HEMA, |
| ratio MI/comonomer (mol/mol) | 1:13, |
| solvent, concentration: | ethanol, 33%, |
| irradiation time (minutes): | 20, |
| Mw of the product according to GPC: | 3547. |

Example C4:

| | |
|---|---|
| macroinitiator ("MI"): | B10 according to EP-A-632 329, |
| comonomer: | PME 400, |
| ratio MI/comonomer (mol/mol) | 1:100, |
| solvent, concentration: | THF, 50%, |
| irriation time (minutes): | 25, |
| Mw of the product according to GPC: | 39 620. |

Example C5:

| | |
|---|---|
| macroinitiator ("MI"): | B6 according to EP-A-632 329, |
| comonomer: | HEMA, |
| ratio MI/comonomer (mol/mol) | 1:10, |
| solvent, concentration: | THF, 50%, |
| irradiation time (minutes): | 25, |
| Mw of the product according to GPC: | 13 590. |

Example C6:

| | |
|---|---|
| macroinitiator ("MI"): | B2 according to EP-A-632 329, |
| comonomer: | 2-HPMA, |
| ratio MI/comonomer (mol/mol) | 1:35, |
| solvent, concentration: | THF, 35%, |
| irradiation time (minutes): | 20, |
| Mw of the product according to GPC: | 26 600. |

Example C7:

| | |
|---|---|
| macroinitiator ("MI"): | B2 according to EP-A-632 329, |
| comonomer: | PME 400, |
| ratio MI/comonomer (mol/mol) | 1:100, |
| solvent, concentration: | THF, 50%, |
| irradiation time (minutes): | 25, |
| Mw of the product according to GPC: | 97 651. |

Example C8:

| | |
|---|---|
| macroinitiator ("MI"): | B10 |
| comonomer: | 2-HPMA, |
| ratio MI/comonomer (mol/mol) | 1:6, |
| solvent, concentration: | THF, 30%, |
| irradiation time (minutes): | 20, |
| Mw of the product according to GPC: | 1900. |

Example C9:

| | |
|---|---|
| macroinitiator ("MI"): | B4 |
| comonomer: | NVP, |
| ratio MI/comonomer (mol/mol) | 1:10, |
| solvent, concentration: | ethanol, 30%, |
| irradiation time (minutes): | 20, |
| Mw of the product according to GPC: | 2960. |

Example C10

2.0 g of macroinitiator from Example B3 are dissolved in 3 ml of dry THllF under nitrogen. 2 g of that solution are mixed with 0.9 g (8 mmol) of freshly distilled NVP and the mixture is gassed with nitrogen for 30 minutes. Clean polypropylene moulds are then filled with the solution under nitrogen (approximately 200 μl of solution per mould), closed and irradiated with UV light (12.5 mW/cm$^2$) for 10 minutes. The moulds containing the highly viscous polymer solution are then freed of THF in a drying cabinet at 40° C. Clear, slightly yellow disks that are soluble in ethanol are obtained. The Mw according to GPC is approximately 5800.

Example C11

In analogy to Example C10, transparent, slightly opaque disks are produced from a mixture of 2.0 g of macroinitiator from Example B3 and 0.9 g (8.15 mmol) of dimethylacrylamide (DMA). The Mw of this tri-block macromer corresponds to 5560 according to GPC.

D-EXAMPLES: PRODUCTION OF CROSSLINKED DISKS OR LENSES

Example D1

2.0 g (0.5 mmol) of macrophotoinitiator according to B6 of EP-A-632 329 are dissolved in 3 ml of ethanol in a 20 ml round-bottomed flask under a nitrogen atmosphere. After the addition of 2.6 g (0.02 mol) of HEMA and 0.4 g (8%) of ethylene glycol dimethaerylate (EGDMA) as crosslinker, the reaction mixture is stirred under nitrogen for 2 hours. The solution is then frozen with liquid nitrogen and degassed under a high vacuum (0.004 mbar) for 15 minutes. The subsequent preparation of the samples and the polymerisation are carried out inside a glove box with the exclusion of oxygen. The reaction mixture is first stirred for 15 minutes, then microfiltered (0.45 μm filter) and subsequently introduced into propylene moulds. Both contact lens moulds and moulds for round disks can be used. The closed moulds are irradiated for 20 minutes at a UV intensity of 12.5 mW/cm$^2$ in a UV oven designed for that purpose. The finished disks or lenses are extracted in ethanol for 24 hours and dried under a high vacuum at 40° C. and 10$^{-3}$ torr. The disks exhibit a modulus of elasticity of 2.1 MPa and an oxygen permeability of 98 barrers.

Example D2

In analogy to Example D1, lenses and disks are produced from 2.0 g (0.5 mmol) of macro-initiator from Example B6 according to EP-A-632 329, 1.3 g (10 mmol) of IEMA, 0.23 g (6.5%) of EGDMA and 3 ml of isopropanol.

Example D3

In analogy to Example D1, lenses are produced from 1 g (0.25 mmol) of macroinitiator from Example B6 according to EP-A-632 329, 1 g (10 mmol) of DMA, 0.2 g (9%) of EGDMA and 2.2 g of isopropanol.

Example D4

In analogy to Example D1, lenses are produced from 3.45 g of macroinitiator from Example B1, 5.95 g of 3-[tris(trimethylsitoxy)sityl]-propyl methacrylate (TRIS), 0.6 g of NVP and 0.5 g (4.75%) of EGDMA, (TRIS and NVP act as solvents for the macroinitiator in question).

Example D5

In analogy to Example D1, disks are produced from 3.92 g (1 mmol) of macroinitiator from Example B3, 3.92 g (8 mmol) of PME 400 and 0.5 g (6%) of EGDMA. THF (5 ml) is used as solvent.

Example D6

In analogy to Example D1, disks are produced from 1.0 g (0.5 mmol) of macroinitiator from Example B10, 0.28 g (2.5 mmol) of NVP, 0.1 g (7.2%) of EGDMA and 1 g of THF.

The following overview shows the properties of the resulting lenses and disks:

| Example | Water absorption (%) | Modulus of elasticity (MPa) | Elongation at break (%) |
|---|---|---|---|
| D2 | 25.2 | 2.8 | 140 |
| D3 | 39.1 | 3.6 | 69 |
| D4 | 5.2 | 0.1 | 97.4 |
| D5 | 41.1 | 0.8 | 144 |
| D6 | 4.0 | 3.0 | 74 |

Example D7

2.5 g (0.3 mmol) of macroinitiator from Example B5 according to EP-A-632 329 are dissolved in 4 ml of dry ethanol under nitrogen. 2.4 g (0.018 mol) of freshly distilled HEMA and 0.4 g (7.5%) of the crosslinker EGDMA are added thereto. The reaction mixture is then stirred under nitrogen for 30 minutes and subsequently gassed with nitrogen for 15 minutes. The solution is then filtered (pore size 0.45 μm) into a bottle. Under nitrogen, clean polypropylene moulds are filled with solution (200 μl per mould), and the moulds are closed and irradiated with UV light for 25 minutes. The moulds are opened and the mould halves, containing the lenses, are placed in an ethanol bath, the lenses being released from the mould halves. The lenses are then extracted in ethanol for a further 24 hours and then dried under a high vacuum ($10^{-4}$ torr). After autoclaving, the lenses are analysed. The lenses have an oxygen permeability of 91.3 barrers and contact angles of 110°(advancing) and 102°(receding).

Example D8

0.16 g of macrophotoinitiator from Example B5 is dissolved, under nitrogen, in 0.82 g of a solution of N-methylpyrrolidone (NMP) in DMSO (70:12). 20 μg of the crosslinker EGDMA are added thereto and the mixture is then gassed with nitrogen for 20 minutes. The solution is then filtered into a bottle (Teflon filter having a pore size of 0.45 μm). Under nitrogen, clean PP moulds are filled with the solution (180–200 per mould), and the moulds are closed and irradiated with UV light (12 mW/cm²) for 30 minutes. The moulds are opened and the mould halves, containing the lenses, are placed in an ethanol bath, the transparent, slightly yellow lenses being released from the mould halves. The lenses are then extracted in ethanol for a further 24 hours and subsequently dried in vacuo.

Example D9

In analogy to Example D8, contact lenses are produced from 0.1 g of macrophotoinitiator from Example B5, 0.5 g of DMSO, 0.4 g of NVP and 20 μg of EGDMA.

Example 10

0.25 g of macrophotoinitiator from Example B8 are dissolved in 0.5 g of dry DMSO under nitrogen. 0.25 g of HEMA and 20 g of the crosslinker EGDMA are added thereto. The mixture is then gassed with nitrogen for 30 minutes. The solution is then filtered (pore size 0.45 μm) and introduced under nitrogen into clean PP moulds. Irradiation and working up are carried out as in Example D8.

The following Table gives information relating to the parameters of the contact lenses so prepared (another term for "strain" being "elongation at break"):

| Example | Water absorption (%) | Strain (%) | Modulus of elasticity (MPa) |
|---|---|---|---|
| D8 | 178 | 490 | 0.04 |
| D9 | 441 | 73 | 0.24 |
| D10 | 19 | 67 | 0.52 |

Example D11

The polymerisation is carried out analogously to Example D8 with the following composition: macroinitiator from Example B4 (20%), DMA (20%), TRIS (5%), EGDMA (5%). Instead of NMP and DMSO, the polymerisation is carried out in ethanol (40%). The lenses exhibit a water absorption of 160% and a modulus of elasticity of 0.34 MPa.

Example D12

2.5 g of the tri-block copolymer described in Example C5—consisting of a central polysiloxane block and two terminal poly-HEMA blocks—are dissolved under dry nitrogen in 3.5 ml of dry THF, and 0.08 g of 2-isocyanatoethyl methacrylate (IEM) and 5 mg of dibutyltin dilaurate are added. The mixture is stirred at 40° C. for 24 hours until all the IEM has reacted (IR spectrum). A contact lens formulation is then prepared by the addition of 0.25 g of DMA and of 150 mg of Irgacure 184 as photoinitiator. According to Example D1, this formulation is used to produce soft contact lenses. After autoclaving, the contact lenses so obtained exhibit an oxygen permeability of 87 barrers.

What is claimed is:

1. An ophthalmic molding, which is the polymerisation product of a polymerisable mixture that comprises the following components:

a) a macromer of formula C

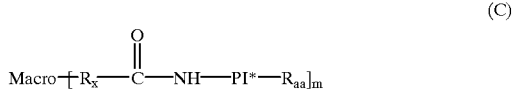

(C)

wherein Macro is an m-valent radical of a polysiloxane or fluorinated polyether from which the number m of groups $R_x$—H has been removed, each $R_x$, independently of the others, is a bond, —O—, —$NRN_N$— or —S— wherein $R_N$ is hydrogen or lower alkyl, PI* is a bivalent benzoyl radical of a photoinitiator comprising a structural unit of the formula

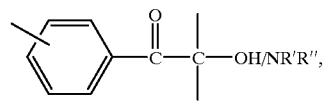

wherein OH/NR'R" indicates that the carbon atom carries either an OH group or an NR'R" group, and R' and R" are each independently of the other linear or branched lower alkyl that is unsubstituted or substituted by $C_1$–$C_4$-alkoxy, $R_{aa}$ is the sp³ carbon radical of the above photoinitiator, and m is an integer from 1 to 100;

b) a copolymerisable hydrophilic vinyl monomer; and c) a crosslinker.

2. An ophthalmic molding according to claim 1, wherein the crosslinker is a oligovinylic compound.

3. An ophthalmic molding according to claim 1, wherein the copolymerisable vinyl monomer comprises a hydroxy or carboxy group and the crosslinker is difunctional compound that is co-reactive with the hydroxy or carboxy groups present in the copolymerisable vinyl monomer.

4. An ophthalmic molding according to claim 1, wherein m in formula (C) is 2 and the two groups bonded to the component "Macro" are terminally bonded to "Macro".

5. An ophthalmic molding according tot wherein Macro in formula (C) is the radical of a polysiloxane or of a fluorinated polyether and the copolymerisable vinyl monomer is a hydrophilic vinyl monomer having a hydroxy or isocyanato reactive group.

6. An ophthalmic molding according to claim 5, wherein the copolymerizable vinyl monomer is a hydroxy-lower alkyl (meth)acrylate or an isocyanato-lower alkyl (meth) acrylate.

7. An ophthalmic molding according to claim 4, wherein Macro in formula (C) is the radical of a polysiloxane or of a fluorinated polyether and the copolymerizable vinyl monomer is a hydrophilic vinyl monomer having no reactive group.

8. An ophthalmic molding according to claim 7, wherein the copolymerizable vinyl monomer is a vinyl-lactam.

9. An ophthalmic molding according to claim 1, wherein the number m of groups in formula (C) that are bonded to the component Macro are bonded exclusively pendantly to Macro.

10. An ophthalmic molding according to claim 1, wherein Macro in formula (C) is a cyclic macromer and the number m of groups that are bonded to the component Macro are bonded pendantly to Macro.

11. An ophthalmic molding according to claim 1, wherein i) component b) comprises a reactive group selected from the group consisting of hydroxy, isocyanate, carboxy and epoxy;

ii) component c) comprises a C-C double bond and a group which is coreactive with the reactive group;

and wherein the polymerisation product is obtained by first copolymerising components a) and b), and then reacting component c) with the reactive groups of the already copolymerised component b) and finally crosslinking the copolymerised component b).

12. A moulding according to claim 1 which is a contact lens.

13. A process for the preparation of an ophthalmic molding according to claim 2, which process comprising the step of copolymerizing the components a), b) and c) to form the ophthalmic molding.

14. A process for preparing an ophthalmic molding according to claim 3, which process comprises the steps of copolymerizing components a) and b), and then crosslinking the copolymerized components with the difunctional component c).

15. A process according to claim 13 for the manufacture of a contact lens, wherein the copolymerization or crosslinking is conducted in a contact lens mould.

* * * * *